(12) United States Patent
Ajima

(10) Patent No.: US 11,051,719 B2
(45) Date of Patent: Jul. 6, 2021

(54) ELECTRONIC DEVICE, GENERATION METHOD, AND GENERATION SYSTEM

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 8 days.

(21) Appl. No.: 16/605,481

(22) PCT Filed: Apr. 10, 2018

(86) PCT No.: PCT/JP2018/015130
§ 371 (c)(1),
(2) Date: Oct. 15, 2019

(87) PCT Pub. No.: WO2018/198765
PCT Pub. Date: Nov. 1, 2018

(65) Prior Publication Data
US 2020/0121223 A1    Apr. 23, 2020

(30) Foreign Application Priority Data
Apr. 25, 2017  (JP) .............................. JP2017-086610

(51) Int. Cl.
| | | |
|---|---|---|
| A61B 5/00 | (2006.01) | |
| A61B 6/03 | (2006.01) | |
| A61B 6/00 | (2006.01) | |
| G01B 21/20 | (2006.01) | |
| A61B 5/11 | (2006.01) | |
| A61B 5/107 | (2006.01) | |
| G01B 3/10 | (2020.01) | |

(52) U.S. Cl.
CPC .......... *A61B 5/1107* (2013.01); *A61B 5/4872* (2013.01); *A61B 5/68* (2013.01); *A61B 6/032* (2013.01); *A61B 6/461* (2013.01); *G01B 21/20* (2013.01); *G01B 3/10* (2013.01)

(58) Field of Classification Search
CPC . A61B 5/107; A61B 2090/367; A61B 5/4872; G06T 7/11; G06T 7/0012; G06T 7/13; G06T 7/80
See application file for complete search history.

(56) References Cited

U.S. PATENT DOCUMENTS

| | | | | |
|---|---|---|---|---|
| 6,546,356 B1 * | 4/2003 | Genest | ...................... | A43D 1/02 702/153 |
| 6,799,066 B2 * | 9/2004 | Steines | .................. | A61B 5/055 382/128 |
| 6,856,824 B1 * | 2/2005 | Wang | .................. | A61B 5/0536 600/425 |
| 7,181,081 B2 * | 2/2007 | Sandrew | ............... | G06T 11/001 348/100 |

(Continued)

FOREIGN PATENT DOCUMENTS

JP    2002-191563 A    7/2002

*Primary Examiner* — Yosef Kassa
(74) *Attorney, Agent, or Firm* — Studebaker & Brackett PC

(57) ABSTRACT

An electronic device includes a measurement unit configured to measure a contour of a body by the electronic device being moved along a surface of the body and a controller configured to generate a three-dimensional image of the body based on the contour. The controller is configured to generate the three-dimensional image by lining up a plurality of first contours measured along a first direction.

14 Claims, 26 Drawing Sheets

(56) References Cited

U.S. PATENT DOCUMENTS

| | | | | |
|---|---|---|---|---|
| 7,239,908 B1* | 7/2007 | Alexander | ............ | A61B 5/055 |
| | | | | 378/21 |
| 7,929,751 B2* | 4/2011 | Zhang | .................... | G06T 7/521 |
| | | | | 382/154 |
| 8,091,967 B2* | 1/2012 | Schweizer | ........... | B60N 2/0232 |
| | | | | 297/284.8 |
| 8,224,089 B2* | 7/2012 | Nielsen | ................... | G06T 17/20 |
| | | | | 382/173 |
| 8,483,425 B2* | 7/2013 | Guo | ......................... | G06T 7/12 |
| | | | | 382/100 |
| 9,129,398 B2* | 9/2015 | Kim | ....................... | G06T 7/246 |
| 9,335,422 B2* | 5/2016 | Oda | ....................... | A61B 6/548 |
| 2014/0121564 A1* | 5/2014 | Raskin | ................. | A61B 5/0022 |
| | | | | 600/587 |

* cited by examiner

FIG. 9

| Record number | Time (s) | Orientation information (°) | Movement information (cm/s²) | Movement amount (cm) |
|---|---|---|---|---|
| R0 | 0 | 0.00 | 0.00 | 0.00 |
| R1 | T1 | 2.05 | 0.85 | 0.42 |
| R2 | T2 | 3.10 | 1.52 | 1.40 |
| R3 | T3 | 5.81 | 2.65 | 3.25 |
| ⋮ | ⋮ | ⋮ | ⋮ | ⋮ |
| Rn | Tn | 360.00 | 0.00 | 82.05 |

FIG. 16

| Time (date and time) | Abdominal girth (cm) | Visceral fat area (cm²) | Subcutaneous fat area (cm²) | Vertical/horizontal length (cm) | Aspect ratio | Food menu | Calories consumed (kcal) | Drink | Health food | Medicine | Calories burned (kcal) | Hours of sleep |
|---|---|---|---|---|---|---|---|---|---|---|---|---|
| 2017-01-01 07:00 | 89 | 110 | 130 | 25/30 | 0.83 | — | | — | | | | |
| 2017-01-01 07:10 | — | — | — | — | — | Ham and egg combo, salad | 500 | Tea, milk (one glass) | | Zetia | | |
| 2017-01-01 12:00 | — | — | — | — | — | Ramen, half-size fried rice | 800 | Water (one glass) | A500ml | | | |
| 2017-01-01 20:00 | — | — | — | — | — | Sukiyaki combo | 1200 | Beer (one bottle) | | | | |
| 2017-01-01 11:59 | — | — | — | — | — | ..... | | ..... | | | 400 | 8 hours |
| ..... | | | | | | | | | | | | |
| 2017-01-07 07:00 | 86 | 100 | 126 | 23/30 | 0.75 | | | | | | | |

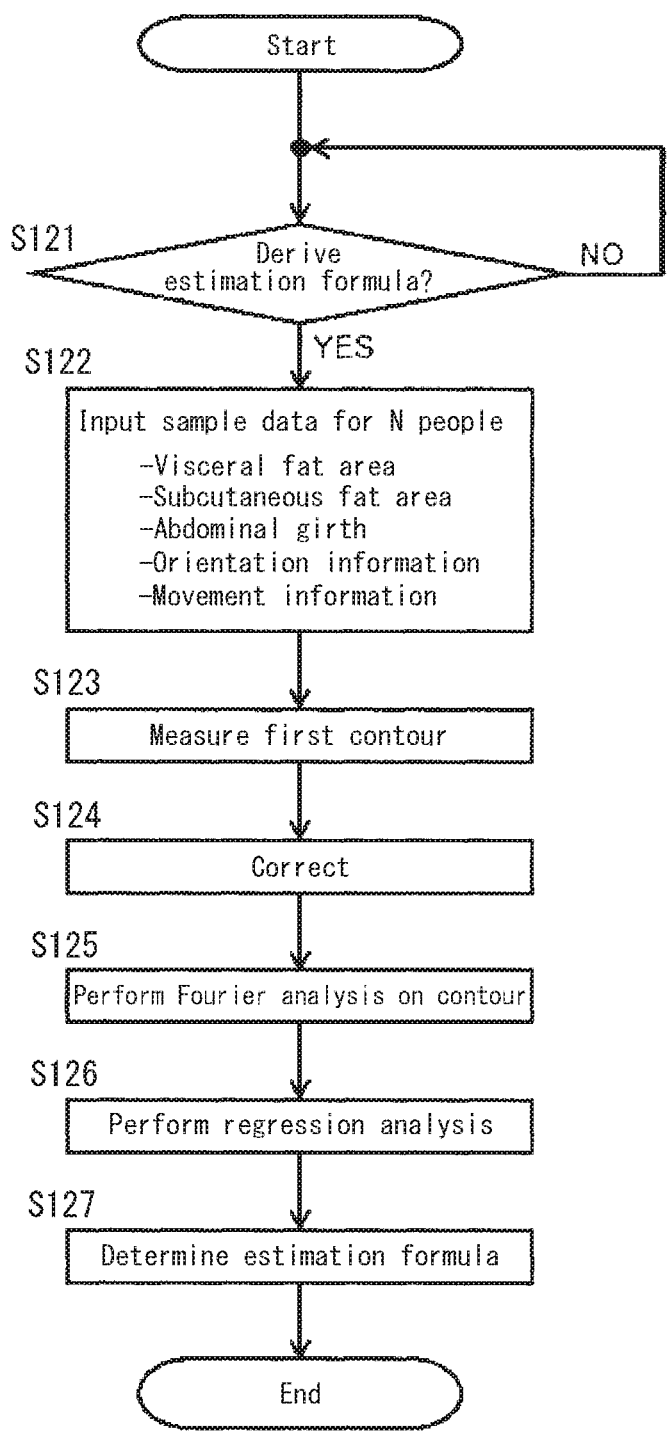

FIG. 23

| Record number | Time (s) | Orientation information (°) | Movement information (movement amount) (cm) |
|---|---|---|---|
| R0 | 0 | 0.00 | 0.00 |
| R1 | T1 | 1.01 | 0.41 |
| R2 | T2 | 1.50 | 0.82 |
| R3 | T3 | 0.51 | 1.23 |
| ⋮ | ⋮ | ⋮ | ⋮ |
| Rn | Tn | 360.00 | 82.05 |

| Record number | Time (s) | Orientation information (°/s) | Orientation (°) | Movement information (movement amount) (cm) |
|---|---|---|---|---|
| R0 | 0 | 0.00 | 0.00 | 0.00 |
| R1 | t1 | 8.22 | 1.37 | 0.42 |
| ⋮ | ⋮ | ⋮ | ⋮ | ⋮ |
| R(n/4) | T(n/4) | 48.72 | 90 | 20.50 |
| ⋮ | ⋮ | ⋮ | ⋮ | ⋮ |
| R(n/2) | T(n/2) | 0.44 | 180 | 41.00 |
| ⋮ | ⋮ | ⋮ | ⋮ | ⋮ |
| R(n/2+a) | T(n/2+a) | 38.21 | 190.12 | 43.15 |

ELECTRONIC DEVICE, GENERATION METHOD, AND GENERATION SYSTEM

CROSS-REFERENCE TO RELATED APPLICATION

The present application claims priority to and the benefit of Japanese Patent Application No. 2017-086610 filed Apr. 25, 2017, the entire contents of which are incorporated herein by reference.

TECHNICAL FIELD

The present disclosure relates to an electronic device, a generation method, and a generation system.

BACKGROUND

Computed tomography (CT) is a known method for measuring the visceral fat area of an abdominal cross-section. A method for visually displaying the visceral fat area measured by CT is also known. For example, an apparatus displays the fat area using a circle.

SUMMARY

An electronic device according to an embodiment includes a measurement unit configured to measure a contour of a body by the electronic device being moved along a surface of the body and a controller configured to generate a three-dimensional image of the body based on the contour. The controller is configured to generate the three-dimensional image by lining up a plurality of first contours measured along a first direction.

A display method according to an embodiment is a display method to be executed by an electronic device and includes measuring a contour of a body by the electronic device being moved along a surface of the body and generating a three-dimensional image of the body by lining up a plurality of first contours measured along a first direction.

A display system according to an embodiment includes a measurement unit configured to measure a contour of a body by a device being moved along a surface of the body and a controller configured to generate a three-dimensional image of the body based on the contour. The controller is configured to generate the three-dimensional image by lining up a plurality of first contours measured along a first direction.

BRIEF DESCRIPTION OF THE DRAWINGS

In the accompanying drawings:

FIG. 9 is an example record of orientation information and movement information according to the first embodiment;

FIG. 16 illustrates example data stored on a storage of the smartphone according to the first embodiment;

FIG. 17 is a flowchart for deriving a visceral fat area estimation formula and a subcutaneous fat area estimation formula;

FIG. 23 is an example record of orientation information and movement information according to the second embodiment;

DETAILED DESCRIPTION

Since the above-described apparatus displays the fat area using a circle, it is difficult for the user (subject) to visually understand the shape of the abdomen. The present disclosure aims to provide an electronic device, a generation method, and a generation system that allow a user to easily understand the shape of the abdomen visually.

Embodiments are described in detail with reference to the drawings.

In the present embodiment, a smartphone 1 is adopted as an example embodiment of an electronic device, and the case of measuring a human body as an example of an object is described. The electronic device is not limited to the smartphone 1, nor is the object limited to a human body. The object may be an animal body. The human body may, for example, include the abdomen of the human. The animal body may, for example, include the torso of the animal.

First Embodiment

The smartphone 1 is an electronic device that includes a first sensor configured to obtain orientation information, a device for obtaining movement information, and a controller 10 configured to calculate the contour of an object. In the present embodiment, the device that obtains movement information includes a second sensor.

Figure 1:
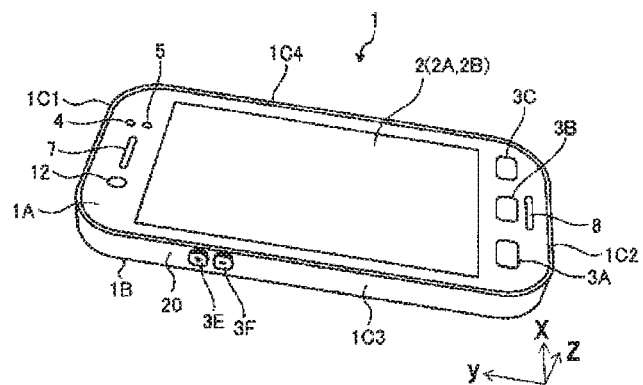
FIG. 1 is a schematic perspective view illustrating the appearance of a smartphone according to a first embodiment.
Figure 2:
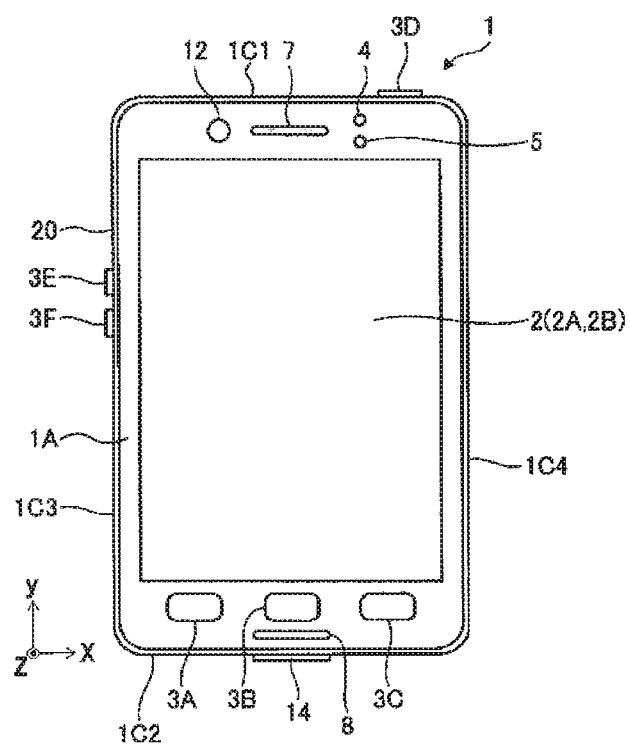
FIG. 2 is a schematic front view illustrating the appearance of the smartphone according to the first embodiment.
Figure 3:
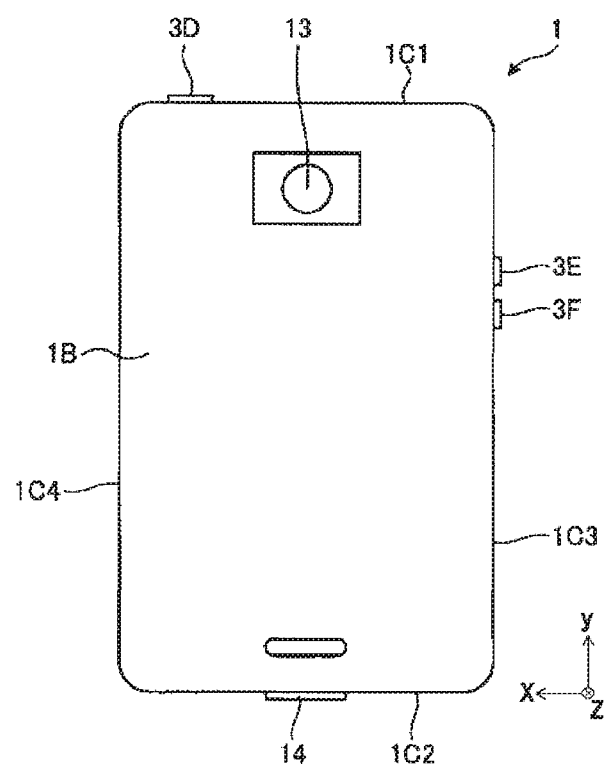
FIG. 3 is a schematic back view illustrating the appearance of the smartphone according to the first embodiment.

The appearance of the smartphone 1 according to the first embodiment is described with reference to FIGS. 1 to 3.

A housing 20 includes a front face 1A, a back face 1B, and side faces 1C1 to 1C4. The front face 1A is the front surface of the housing 20. The back face 1B is the back surface of the housing 20. The side faces 1C1 to 1C4 are side surfaces that connect the front face 1A and the back face 1B. The side faces 1C1 to 1C4 may be collectively referred to below as the side faces 1C without further distinction.

On the front face 1A, the smartphone 1 includes a touchscreen display 2, buttons 3A to 3C, an illuminance sensor 4, a proximity sensor 5, a receiver 7, a microphone 8, and a camera 12. The smartphone 1 includes a camera 13 on the back face 1B. The smartphone 1 also includes buttons 3D to 3F and a connector 14 on the side faces 1C. The buttons 3A to 3F may be collectively referred to below as the buttons 3 without further distinction.

The touchscreen display 2 includes a display 2A and a touchscreen 2B. The display 2A is provided with a display device such as a liquid crystal display, an organic electro-luminescence panel, or an inorganic electro-luminescence panel. The display 2A functions as a display for displaying characters, images, symbols, graphics, and the like.

The touchscreen 2B detects contact on the touchscreen 2B by a finger, stylus pen, or other such object. The touchscreen 2B can detect the position at which a plurality of fingers, a stylus pen, or another object contacts the touchscreen 2B.

Any detection system may be used in the touchscreen 2B, such as a capacitive system, a resistive film system, a surface acoustic wave system (or an ultrasonic wave system), an infrared system, an electromagnetic induction system, or a load detection system. In a capacitive system, contact and proximity of an object such as a finger or stylus pen can be detected.

Figure 4:
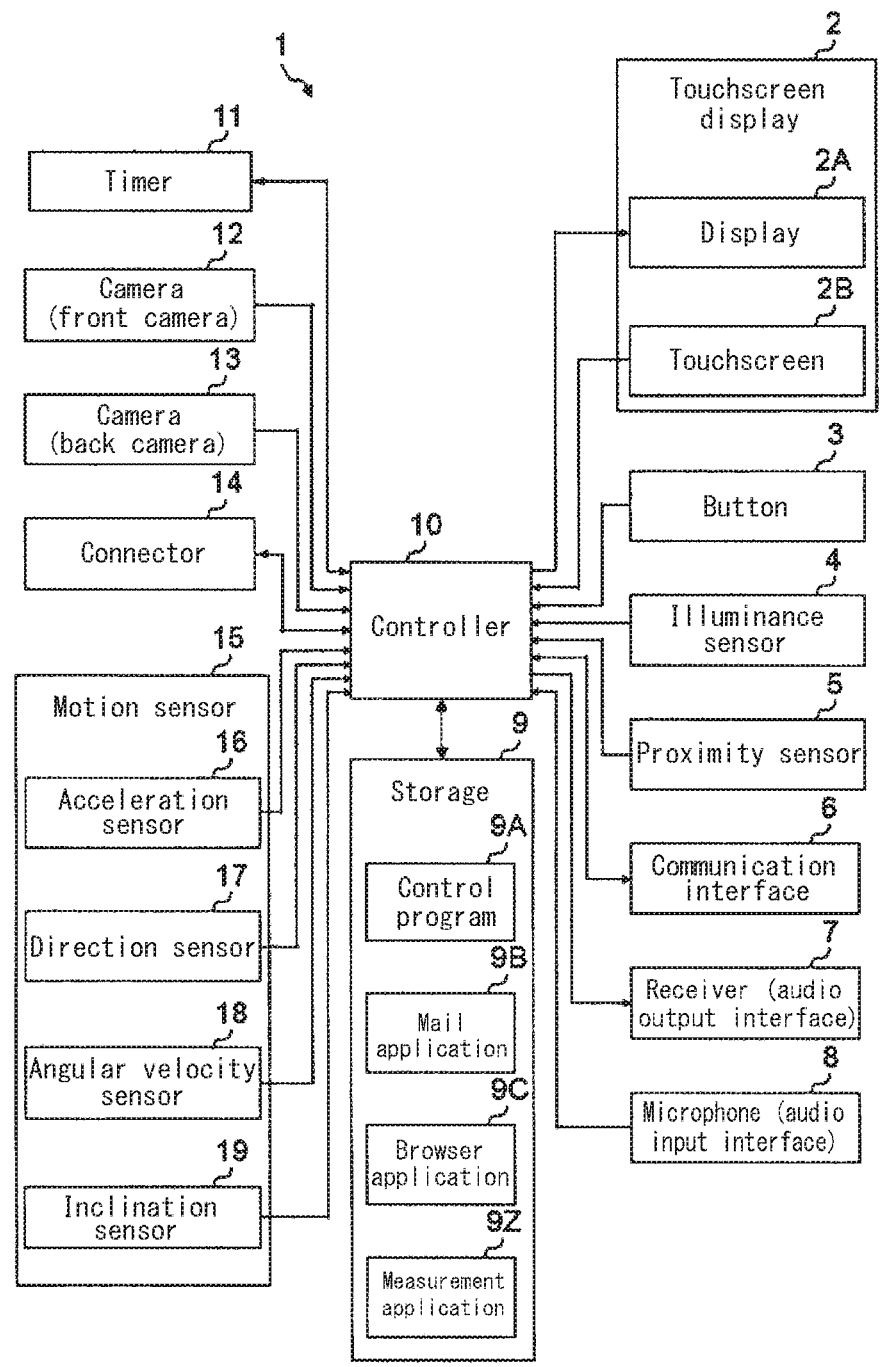
FIG. 4 is a schematic block diagram illustrating the functions of the smartphone according to the first embodiment.

FIG. 4 is a block diagram illustrating the configuration of the smartphone 1. The smartphone 1 includes the touchscreen display 2, buttons 3, the illuminance sensor 4, a proximity sensor 5, a communication interface 6, the receiver 7, the microphone 8, a storage 9, the controller 10, a timer 11, the cameras 12 and 13, the connector 14, and a motion sensor 15.

As described above, the touchscreen display 2 includes a display 2A and a touchscreen 2B. The display 2A displays characters, images, symbols, graphics, and the like. The touchscreen 2B receives input of contact on a receiving area. In other words, the touchscreen 2B detects contact. The controller 10 detects a gesture on the smartphone 1. The controller 10 works together with the touchscreen 2B to detect an operation (gesture) on the touchscreen 2B (touchscreen display 2). The controller 10 also works together with the touchscreen 2B to detect an operation (gesture) on the display 2A (touchscreen display 2).

The buttons 3 are operated by the user. The buttons 3 include button 3A to button 3F. The controller 10 works together with the buttons 3 to detect an operation on the buttons. Examples of operations on the buttons include a click, a double-click, a push, a long push, and a multi-push.

For example, the buttons 3A to 3C may be a home button, a back button, or a menu button. In the present embodiment, touch-sensor buttons are used as the buttons 3A to 3C. The button 3D may, for example, be a power button for the smartphone 1. The button 3D may also function as a button to engage/release a sleep mode. The buttons 3E and 3F may, for example, be volume buttons.

The illuminance sensor 4 detects illuminance. The illuminance may, for example, be the intensity of light, brightness, or luminance. The illuminance sensor 4 may, for example, be used to adjust the luminance of the display 2A.

The proximity sensor 5 detects the presence of a nearby object without contact. The proximity sensor 5 may, for example, detect that the touchscreen display 2 has been brought close to a face.

The communication interface 6 communicates wirelessly. The communication method of the communication interface 6 is prescribed by a wireless communication standard. For example, a cellular phone communication standard such as 2G, 3G, or 4G may be used as the wireless communication standard. Examples of cellular phone communication standards include Long Term Evolution (LTE), W-CDMA, CDMA2000, PDC, Global System for Mobile communications (GSM® (GSM is a registered trademark in Japan, other countries, or both)), and Personal Handy-phone System (PHS). Examples of wireless communication standards include Worldwide Interoperability for Microwave Access (WiMAX), IEEE802.11, Bluetooth® (Bluetooth is a registered trademark in Japan, other countries, or both), IrDA, and NFC. The communication interface 6 may support one or more of the aforementioned communication standards.

The receiver 7 outputs an audio signal, transmitted from the controller 10, as sound. The microphone 8 converts sound from the user or another source to an audio signal and transmits the audio signal to the controller 10. The smartphone 1 may include a speaker instead of the receiver 7.

The storage 9 functions as a memory storing programs and data. The storage 9 may also be used as a memory for storing results of processing by the controller 10 temporarily. The storage 9 may include any appropriate storage device, such as a semiconductor storage device or a magnetic storage device. The storage 9 may also include a plurality of types of storage devices. The storage 9 may include a combination of a portable storage medium, such as a memory card, and an apparatus for reading the storage medium.

The programs stored on the storage 9 include applications that run in the foreground or the background and a control program that supports operations of the applications. The applications may, for example, display a predetermined screen on the display 2A and cause the controller 10 to execute processing in accordance with a gesture detected by the touchscreen 2B. The control program may, for example, be an operating system (OS). The applications and the control program may be installed on the storage 9 through wireless communication by the communication interface 6 or from a storage medium.

The storage 9 for example stores a control program 9A, a mail application 9B, a browser application 9C, and a measurement application 9Z. The mail application 9B provides e-mail functions for actions such as creating, sending, receiving, and displaying e-mail. The browser application 9C provides a Web browsing function to display Web pages. The measurement application 9Z provides a function for the user to measure the contour of an object with the smartphone 1 and generate a three-dimensional image.

The control program 9A provides functions related to various types of control which enable the smartphone 1 to operate. The control program 9A may, for example, place a phone call by controlling components such as the communication interface 6, receiver 7, and microphone 8. The functions provided by the control program 9A may be used in combination with functions provided by other programs, such as the mail application 9B.

The controller 10 may, for example, be a central processing unit (CPU). The controller 10 may be a system-on-a-chip (SoC) or other type of integrated circuit in which other components, such as the communication interface 6, are integrated. The controller 10 may be configured by combining a plurality of integrated circuits. The controller 10 functions as a control unit for implementing a variety of functions by comprehensively controlling operations of the smartphone 1.

Specifically, the controller 10 refers as necessary to data stored in the storage 9. The controller 10 executes commands included in the programs stored in the storage 9 to control components such as the display 2A, the communication interface 6, and the motion sensor 15, thereby implementing various functions. The controller 10 implements various functions by executing commands included in the measurement application 9Z stored in the storage 9. The controller 10 can change the control in response to detection results from various detectors, such as the touchscreen 2B, buttons 3, and motion sensor 15. In the present embodiment, the entire controller 10 functions as a control unit. The controller 10 calculates a contour of an object based on orientation information acquired by the first sensor and movement information acquired by the second sensor.

The timer 11 outputs a clock signal with a preset frequency. The timer 11 receives an instruction for a timer operation from the controller 10 and outputs the clock signal to the controller 10. The first sensor and the second sensor acquire orientation information and movement information multiple times in accordance with clock signals input through the controller 10. The timer 11 may be provided externally to the controller 10 or may be included in the controller 10, as illustrated below in FIG. 21.

The camera 12 is a front camera that images an object facing the front face 1A. The camera 13 is a back camera that images an object facing the back face 1B.

The connector 14 is a terminal to which another apparatus connects. The connector 14 of the present embodiment also functions as a communication interface for communication between the smartphone 1 and another apparatus over a connection object connected to the terminal. The connector 14 may be a general-purpose terminal such as a universal serial bus (USB), high-definition multimedia interface (HDMI® (HDMI is a registered trademark in Japan, other countries, or both)), mobile high-definition link (MHL), Light Peak, Thunderbolt, local area network connector, or an earphone microphone connector. The connector 14 may be designed as a dedicated terminal, such as a dock connector. Examples of the apparatuses that connect to the connector 14 include a charger, an external storage, a speaker, a communication apparatus, and an information processing apparatus.

The motion sensor 15 detects a motion factor. This motion factor is mainly processed as a control factor of the smartphone 1, i.e. the electronic device. The control factor is a factor indicating the status of the electronic device and is processed by the controller 10. The motion sensor 15 functions as a measurement unit for measuring the contour of the user's body. The motion sensor 15 of the present embodiment includes an acceleration sensor 16, a direction sensor 17, an angular velocity sensor 18, and an inclination sensor 19. The combined output of the acceleration sensor 16, direction sensor 17, angular velocity sensor 18, and inclination sensor 19 can be used. By processing the combined output of the motion sensor 15, the controller 10 can execute processing that amply reflects the movement of the smartphone 1, i.e. the electronic device.

In the present embodiment, the first sensor obtains the orientation information of the smartphone 1, i.e. the electronic device. The orientation information of the smartphone 1 is outputted from the first sensor. The orientation information of the smartphone 1 is related to the direction in which the smartphone 1 is facing. The orientation information of the smartphone 1 for example includes the direction of the earth's magnetism, the inclination relative to the earth's magnetism, the direction of the rotation angle, the change in the rotation angle, the direction of gravity, and the inclination relative to the direction of gravity.

The orientation of the smartphone 1 refers to the direction of a normal to the surface of the housing 20 that is opposite the object when the contour of the object is being measured. The surface of the housing 20 that is opposite the object may be any surface whose orientation can be detected by the first sensor. This surface may be any of the front face 1A, the back face 1B, and the side faces 1C1 to 1C4.

In the present embodiment, any of the direction sensor 17, the angular velocity sensor 18, and the inclination sensor 19 may be used as the first sensor. As described below, the smartphone 1 measures the contour of the body in two different directions, a first direction and a second direction. Different sensors may be used as the first sensor in accordance with the direction in which the contour is measured.

The direction sensor 17 is a sensor that detects the orientation of the earth's magnetism. When the direction sensor 17 is used as the first sensor, the component when the orientation of the smartphone 1 is projected onto a plane parallel to the ground is the orientation information acquired by the direction sensor 17. The orientation information acquired by the direction sensor 17 is the direction of the smartphone 1. The direction of the smartphone 1 can be acquired as 0° to 360° orientation information. For example, the orientation information that is acquired is 0° when the smartphone 1 is facing north, 90° when facing east, 180° when facing south, and 270° when facing west. When the direction sensor 17 is used as the first sensor, the orientation information can be acquired accurately if the contour of the measured object is parallel to the ground. For example, when the abdomen of the body serving as the object is measured circumferentially (the below-described first direction) while standing, the direction sensor 17 can be used as the first sensor.

The direction sensor 17 outputs the detected orientation of the earth's magnetism. For example, when the orientation of the earth's magnetism is output as a motion factor, the controller 10 can execute processing using this motion factor as a control factor that reflects the direction in which the smartphone 1 faces. For example, when the change in the orientation of the earth's magnetism is output as a motion factor, the controller 10 can execute processing using this motion factor as a control factor that reflects the change in the orientation of the smartphone 1.

The angular velocity sensor 18 detects the angular velocity of the smartphone 1. The angular velocity sensor 18 can acquire the angular velocity of the smartphone 1 as orientation information. The controller 10 calculates the orientation of the smartphone 1 by time integrating the acquired angular velocity once. The calculated orientation of the smartphone 1 is an angle relative to an initial value at the start of measurement.

The angular velocity sensor 18 outputs the detected angular velocity. For example, when the orientation of the angular velocity is output as a motion factor, the controller 10 can execute processing using this motion factor as a control factor that reflects the rotation direction of the smartphone 1. For example, when the magnitude of the angular velocity is output, the controller 10 can execute processing using this magnitude as a control factor that reflects the rotation amount of the smartphone 1.

The inclination sensor 19 detects the gravitational acceleration acting on the smartphone 1. The inclination sensor 19 can acquire the gravitational acceleration of the smartphone 1 as orientation information. For example, with the inclination sensor 19, the smartphone 1 can acquire −9.8 $m/s^2$ to 9.8 $m/s^2$ as the orientation information. The acquired orientation information is 9.8 $m/s^2$ when, for example, the y-axis direction of the smartphone 1 illustrated in FIG. 1 is the same as the direction of gravity and is −9.8 $m/s^2$ in the opposite case. When the y-axis direction is perpendicular to the direction of gravity, the acquired orientation information is 0 $m/s^2$. When the inclination sensor 19 is used as the first sensor, the orientation information can be acquired accurately if the contour of the measured object is substantially perpendicular to the ground. For example, when the body serving as the object is measured in the height direction (the below-described second direction) while standing, the inclination sensor 19 can be used as the first sensor.

The inclination sensor 19 outputs the detected inclination. For example, when the inclination relative to the direction of gravity is output as a motion factor, the controller 10 can execute processing using this motion factor as a control factor that reflects the inclination of the smartphone 1.

In some cases, the controller 10 calculates the orientation based on the orientation information of the smartphone 1. For example, the above-described angular velocity sensor 18 acquires the angular velocity as orientation information. Based on the acquired angular velocity, the controller 10 calculates the orientation of the smartphone 1. As another example, the above-described inclination sensor 19 acquires the gravitational acceleration as orientation information. Based on the acquired gravitational acceleration, the controller 10 calculates the orientation of the smartphone 1 relative to the direction of gravity.

A combination of motion sensors 15 described above can be used as the first sensor. By processing a combination of orientation information from a plurality of motion sensors, the controller 10 can more accurately calculate the orientation of the smartphone 1, i.e. the electronic device.

In the present embodiment, the device for obtaining movement information of the electronic device is the second sensor. The second sensor obtains movement information of the smartphone 1, i.e. the electronic device. The movement information of the smartphone 1 is outputted from the second sensor. The movement information of the smartphone 1 is related to the movement amount of the smartphone 1. The movement information of the smartphone 1 for example includes acceleration, speed, and movement amount.

In the present embodiment, the movement amount of the smartphone 1 is the movement amount of a reference position of the housing 20 in the smartphone 1. The reference position of the housing 20 may be any position detectable by the second sensor, such as the surface of the side face 1C1.

In the present embodiment, the acceleration sensor 16 can be used in the second sensor. The acceleration sensor 16 detects the acceleration acting on the smartphone 1. The acceleration sensor 16 can acquire the acceleration of the smartphone 1 as movement information. The controller 10 calculates the movement amount of the smartphone 1 by time integrating the acquired acceleration twice.

The acceleration sensor 16 outputs the detected acceleration. For example, when the direction of the acceleration is output, the controller 10 can execute processing using this direction as a control factor that reflects the direction in which the smartphone 1 is moving. For example, when the magnitude of the acceleration is output, the controller 10 can execute processing using this magnitude as a control factor that reflects the speed at which the smartphone 1 is moving and the movement amount.

The controller 10 generates a wire frame image of the object by calculating the contour of the object. The contour of the object is calculated based on the orientation information and movement information acquired by the first sensor and the second sensor. In some cases, the controller 10 calculates the orientation and the movement amount during the calculation process. The controller 10 generates a three-dimensional image of the object based on the generated wire frame image. The three-dimensional image is, for example, generated as a three-dimensional wire frame image.

A sensor that can detect motion factors in three axial directions is used in the above-described motion sensor 15. The three axial directions detected by the motion sensor 15 of the present embodiment are substantially orthogonal to each other. The x-direction, y-direction, and z-direction illustrated in FIGS. 1 to 3 correspond to the three axial directions of the motion sensor 15. The three axial directions need not be orthogonal to each other. In a motion sensor 15 in which the three directions are not orthogonal to each other, motion factors in three orthogonal directions can be calculated. The direction serving as a reference may differ for each motion sensor 15. In the present embodiment, each motion sensor 15 is not necessarily a three-axis sensor. The controller 10 can calculate the contour with the orientation information in one axial direction and the movement information in one axial direction.

The first sensor and the second sensor may use any of the above-described motion sensors 15 or another motion sensor.

A portion or all of the programs stored in the storage 9 in FIG. 4 may be downloaded by the communication interface 6 from another apparatus by wireless communication. A portion or all of the programs stored in the storage 9 in FIG. 4 may also be stored in a non-transitory storage medium that is readable by a reading apparatus included in the storage 9. A portion or all of the programs stored in the storage 9 in FIG. 4 may also be stored in a non-transitory storage medium that is readable by a reading apparatus connected to the connector 14. Examples of the storage medium include flash memory, a hard disk drive (HDD®), a compact disk (CD), a digital versatile disc (DVD®), and a Blu-ray® disc (HDD, DVD, and Blu-ray are registered trademarks in Japan, other countries, or both).

The configuration of the smartphone 1 illustrated in FIGS. 1 to 4 is only an example and may be changed as necessary without departing from the scope of the present disclosure. For example, the number and type of buttons 3 are not limited to the example in FIG. 1. Instead of including the buttons 3A to 3C, for example, the smartphone 1 may include buttons arranged as a numeric keypad, a QWERTY keyboard, or another arrangement as buttons for operating the screen. In order to operate the screen, the smartphone 1 may include just one button or may lack buttons altogether. In the example in FIG. 4, the smartphone 1 includes two cameras, but the smartphone 1 may include just one camera or may lack cameras altogether. The illuminance sensor 4 and the proximity sensor 5 may be configured by one sensor. In the example illustrated in FIG. 4, four types of sensors are provided to acquire the orientation information and the movement information of the smartphone 1, i.e. the electronic device. The smartphone 1 need not include all of these sensors, however, and may include other types of sensors.

Next, the method of measuring the object using the smartphone 1 according to the present embodiment is described. The user moves the smartphone 1 along the object while the measurement function is activated in the measurement application 9Z. The user may move the smartphone 1 in a first direction and in a second direction different from the first direction. In the present embodiment, the first direction is the circumferential direction of the body (torso). In the present embodiment, the second direction is the height direction.

Figure 5:
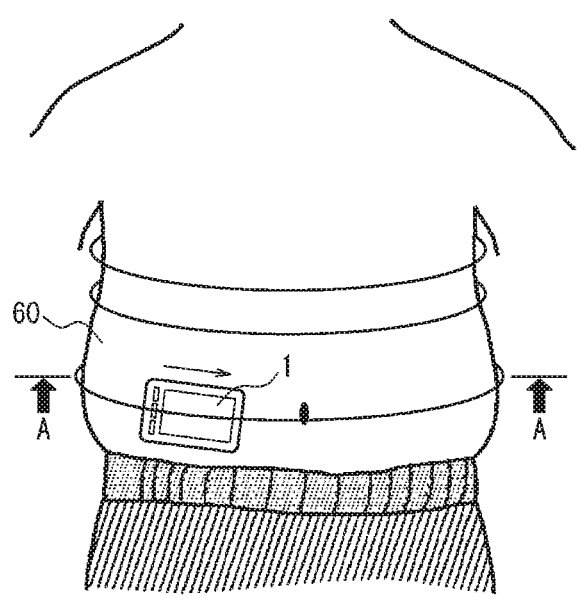
FIG. 5 is a schematic diagram illustrating measurement of the contour of an object according to the first embodiment.
Figure 6:
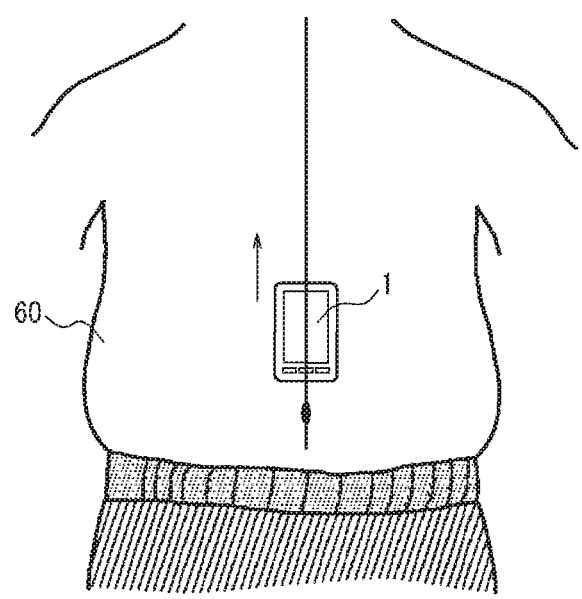
FIG. 6 is a schematic diagram illustrating measurement of the contour of an object according to the first embodiment.

FIGS. 5 and 6 are schematic diagrams illustrating measurement of the contour of an object according to the present embodiment. FIG. 5 schematically illustrates measurement of the contour in the first direction. As illustrated in FIG. 5, the user measures the contour of the object in the first direction by moving (scanning) the smartphone 1 along the circumferential direction of the body. The contour measured along the first direction is referred to as the "first contour" in the present disclosure. As illustrated in FIG. 5, the user can measure the contour in the first direction multiple times while changing the height. The user can, for example, measure a plurality of first contours by measuring the first contour at a height passing through the umbilicus (belly button) and then increasing the height from the height passing through the umbilicus by a predetermined distance (such as 5 cm or 10 cm) at a time, moving the smartphone in the first direction at each height.

FIG. 6 schematically illustrates measurement of the contour in the second direction. As illustrated in FIG. 6, the user measures the contour of the object in the second direction by moving the smartphone 1 along the height direction of the body. The user may, for example, move the smartphone 1 along the midline of the body. The contour measured along the second direction is referred to as the "second contour" in the present disclosure.

As is clear from FIGS. 5 and 6, the first direction and the second direction may be substantially orthogonal. Here, "substantially orthogonal" includes the extent of intersection between the circumferential direction of the body and the height direction. One of the plurality of first contours and the second contour pass through the umbilicus. Accordingly, this first contour and the second contour are substantially orthogonal at the umbilicus.

Figure 7:
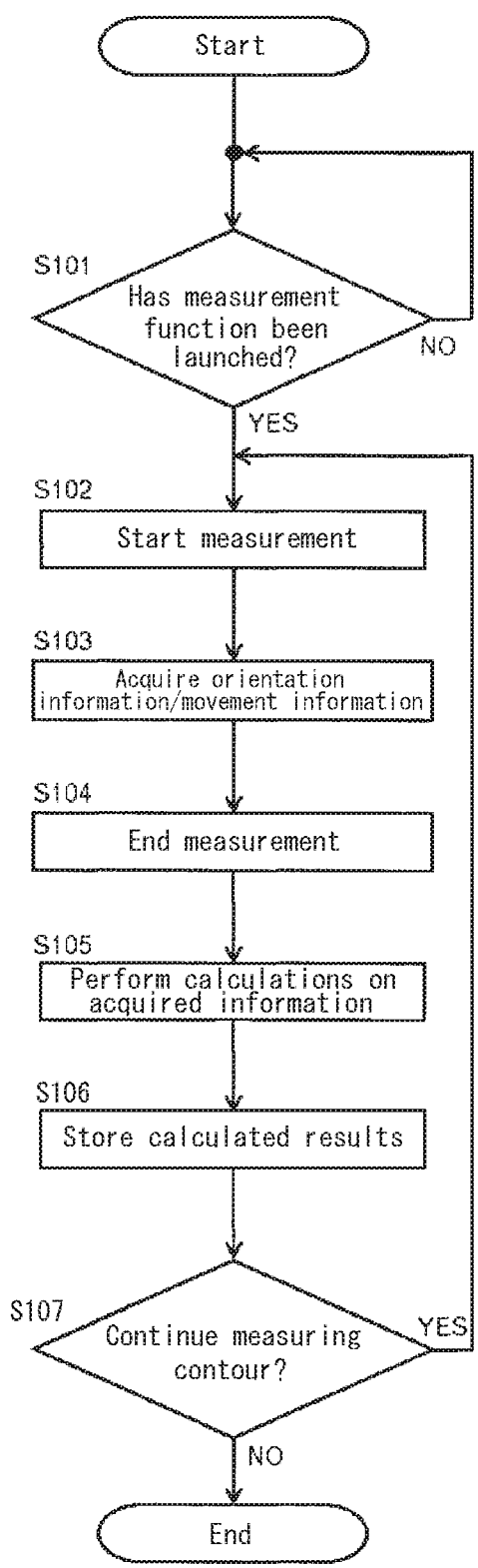
FIG. 7 is a flowchart for measuring the contour of an object according to the first embodiment.

FIG. 7 is a flowchart for measuring the contour of an object according to the present embodiment. Here, the case of measuring the first contour is described.

In step S101, the user activates the measurement function in the measurement application 9Z. Next, measurement begins in step S102. At the start of measurement, the smartphone 1 is placed against the surface of the abdomen 60 at any position where the contour of the object is to be measured. For example, the smartphone 1 is placed against the surface of the abdomen 60 at the height of the user's umbilicus (the position indicated by line A-A in FIG. 5). As long as measurement of the contour of the object is not impeded, the smartphone 1 may be contacted to the surface of the abdomen 60 directly or with clothing therebetween. The measurement start position may be anywhere along the abdominal A-A position. To start measurement, the user performs a preset start action on the smartphone 1. The preset start action may be an action such as pushing one of the buttons 3 of the smartphone 1 or tapping a particular position on the touchscreen 2B. The surface that opposes the abdominal surface may be any of the front face 1A, back face 1B, and side faces 1C1 to 1C4 of the smartphone 1. For operability, however, the back face 1B is the opposing face in the present embodiment.

In step S103, the user moves the smartphone 1 along the surface at the A-A position of the abdomen 60 once around the abdomen 60. If the user moves the smartphone 1 at a constant speed while keeping the smartphone 1 against the surface of the abdomen 60, the interval between acquisition of various information becomes constant, which increases the accuracy of contour measurement.

In step S103, under conditions programmed in advance, the direction sensor 17 acquires orientation information and the acceleration sensor 16 acquires movement information. The orientation information and movement information are acquired multiple times. The orientation information and the movement information are acquired in accordance with the clock signal output from the timer 11. The acquisition cycle for each type of information may be selected in accordance with the size (i.e. circumferential length) and/or complexity of the contour of the measured object. The acquisition cycle of information may, for example, be selected from among a sampling frequency of 5 Hertz (Hz) to 60 Hz. The acquired orientation information and movement information are temporarily stored inside the smartphone 1. This measurement is continuously made from the start of step S102 until the end of step S104.

After moving the smartphone 1 once around the abdomen 60 while keeping the smartphone 1 against the abdomen 60, the user performs an end action, set in advance, on the smartphone 1 to end measurement (step S104). The end action set in advance may be an action such as pushing one of the buttons 3 of the smartphone 1 or tapping a particular position on the touchscreen 2B. Alternatively, the smartphone 1 may automatically end measurement by recognizing one circumference when the orientation information acquired by the direction sensor 17 of the smartphone 1 matches the orientation information at the start of measurement or changes by 360° from the orientation information at the start of measurement. In the case of automatic recognition, the user need not perform the end action, thereby simplifying measurement.

In step S105, calculations are performed on the orientation information and the movement information acquired in step S103. The controller 10 performs these calculations. The controller 10 calculates the contour and abdominal girth of the object. Details on the calculations in step S105 are provided below.

In step S106, the smartphone 1 stores the results of the calculations performed in step S105 in the storage 9.

In step S107, the smartphone 1 judges whether to continue measuring the contour based on user operation input. When contour measurement is to be continued (step S107: YES), the smartphone 1 proceeds to step S102. In this case, the user can measure the first contour by placing the smartphone 1 against the abdomen 60 at a different height and moving the smartphone 1 in the first direction. After measuring the first contour at the height of the umbilicus, the user can measure the first contour at a position that is a predetermined distance higher than the umbilicus and then repeat the process to measure a plurality of first contours at different heights. The smartphone 1 can estimate the distance (the displacement in the height direction) from the umbilicus of each of the first contour in accordance with the order of measurement.

When contour measurement is not to be continued (step S107: NO), the smartphone 1 ends the processing flow.

The smartphone 1 can measure the second contour with a similar procedure as in FIG. 7. In this case, the user can measure the second contour by placing the smartphone 1 against the umbilicus and then moving the smartphone 1 in the second direction along the midline, for example. The smartphone 1 can thereby recognize the measurement start position during measurement of the second contour as the position of the umbilicus. After measuring the first contour, the user may provide input to the smartphone 1 indicating measurement of the second contour before measuring the second contour. The smartphone 1 can thereby process the contour measured after the input as the second contour.

In the present embodiment, the back face 1B of the smartphone 1 is placed against the abdomen and moved in the y-axis direction. In this case, the direction sensor 17 may be a uniaxial sensor capable of measuring the orientation in the y-axis direction of the smartphone 1. The acceleration sensor 16 may be a uniaxial sensor capable of measuring the movement amount in the y-axis direction.

Next, the method of calculating the contour of the object is described with reference to FIGS. 8A to 10, taking the smartphone 1 as an example. While the method of calculating the first contour is described here, the second contour may be calculated with a similar method.

Figure 8A:
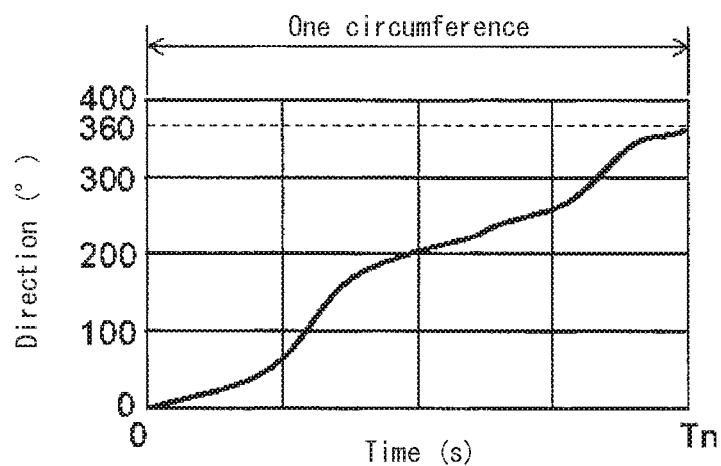
FIGS. 8A and 8B illustrate an example of orientation and movement amount according to the first embodiment.
Figure 8B:
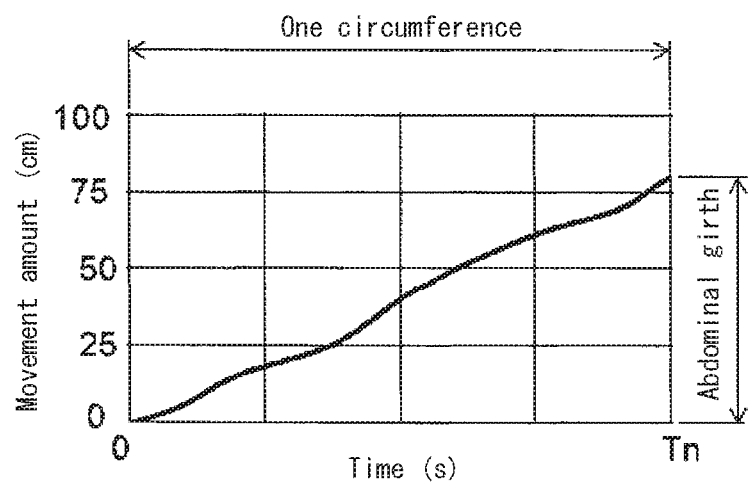

FIGS. 8A and 8B illustrate an example of orientation and movement amount according to an embodiment.

The horizontal axis in FIGS. 8A and 8B indicates the time from the start to the end of measurement. Time is counted by the clock signal output by the timer 11. When the circumference of the abdomen is measured in Tn seconds (s), the start of measurement is at 0 s and the end of measurement at Tn s. Over predetermined acquisition cycles, the smartphone 1 acquires the orientation information and movement information from 0 s to Tn s.

In FIG. 8A, the horizontal axis represents time, and the vertical axis represents the direction of the smartphone 1. The direction of the smartphone 1 on the horizontal axis is orientation information acquired by the direction sensor 17. The direction sensor 17 is adopted as the first sensor in the present embodiment. Hence, the orientation information is the direction of the smartphone 1. The direction of the smartphone 1 is represented as an angle from 0° to 360°. The direction of the smartphone 1 is determined to have completed one circumference upon changing 360° from the initial orientation of measurement. In the present embodiment, the initial orientation of measurement is set to 0° for ease of understanding, making the orientation 360° after one circumference.

In FIG. 8B, the horizontal axis represents time, and the vertical axis represents the movement amount of the smartphone 1. The movement amount of the smartphone 1 on the vertical axis is calculated based on the movement information acquired by the acceleration sensor 16. The movement information of the smartphone 1 in the present embodiment is acceleration data acquired by the acceleration sensor 16. The movement amount is calculated by the controller 10 by time integrating the acceleration data twice. When the acceleration data includes a large amount of noise, digital filtering may be performed. The digital filter may, for example, be a low pass filter or a band pass filter. The movement amount of the smartphone 1 at the end of measurement corresponds to the circumference of the measured object, i.e. the abdominal girth in the present embodiment. The abdominal girth may be calculated taking into account the arrangement of the acceleration sensor 16 within the smartphone 1. In other words, the abdominal girth may be calculated accurately in the present embodiment by correction of the movement amount taking into consideration the interval between the acceleration sensor 16 and the back face 1B, which is the opposing surface placed against the surface of the abdomen 60.

In the present embodiment, the case of measuring direction and the movement amount during the same time Tn has been illustrated, but the direction and the movement amount may be measured in different times Ta and Tb. In that case, the horizontal axis of FIG. 8A may use a normalized time 0-1 normalized by Ta, the horizontal axis of FIG. 8B may use a normalized time 0-1 normalized by Tb, and the numerical values on each horizontal axis may be aligned.

FIG. 9 is an example record formed by acquired information.

The record number at the start of measurement is R0, and the record number at the end of measurement is Rn. In each record, orientation information and movement information corresponding to time are stored as a pair. Furthermore, the movement amount calculated based on the movement information is stored in each record. In the present embodiment, which uses the direction sensor 17, the orientation information is the direction faced by the smartphone 1. The direction and movement amount, which are information calculated based on the pair of orientation information and movement information, are acquired at the same time in FIGS. 8A and 8B. The direction and movement amount, which are information calculated based on the pair of orientation information and movement information, may be acquired at the same standardized time. The time intervals between the records need not be equal intervals. A pair of records may be information acquired at the same time, or the acquisition times may differ. When the acquisition times differ, the controller 10 may take the time difference into account.

Figure 10:
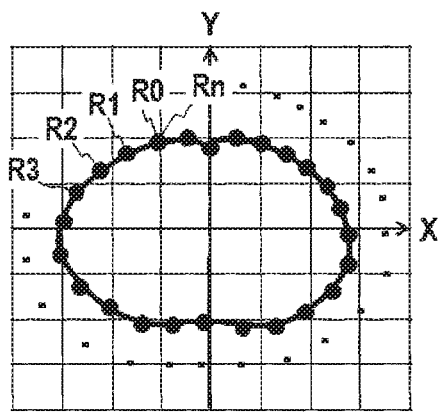
FIG. 10 illustrates the contour of an object calculated in the first embodiment.

FIG. 10 illustrates a calculated first contour of the object.

The first contour of the object can be calculated by plotting the acquired records R0 to Rn in order in accordance with orientation and movement amount. The labels R0 to Rn in FIG. 10 indicate the corresponding record numbers. The points on the solid line indicate the positions of the records. The line actually includes many more points, but some of the points are omitted to clarify the drawing.

The first contour is calculated as follows. First, R0 is set at any point. Next, the position of R1 is calculated from the amount of change in the movement amount between record R0 and record R1 and the orientation information of record R1. Next, the position of R2 is calculated from the amount of change in the movement amount between record R1 and record R2 and the orientation information of record R2. This calculation is made up to Rn. By connecting the positions in order from the position of R0 to the position of Rn, the first contour is calculated and then displayed.

Figure 11:
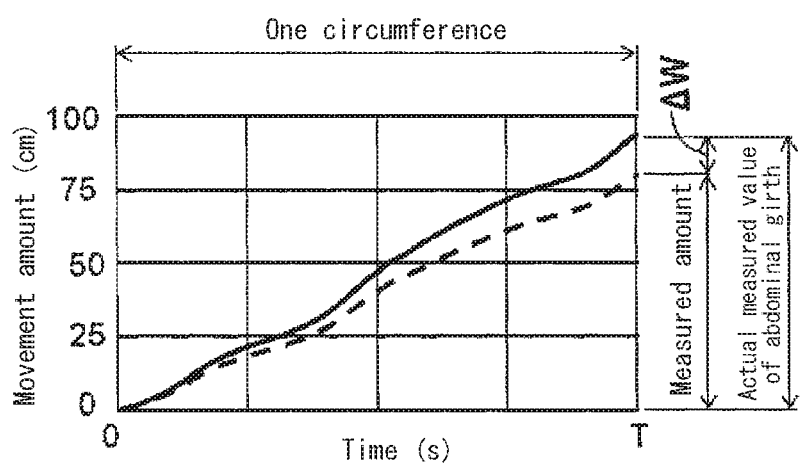
FIG. 11 illustrates correction using an actual measured value according to the first embodiment.

FIG. 11 illustrates correction using an actual measured value according to the first embodiment.

In the above embodiment, the movement information acquired by the acceleration sensor 16 is used to calculate the first contour. The actual measured circumference of the object as measured in advance by other means, however, may be used. In FIG. 11, the horizontal axis represents time, and the vertical axis represents the movement amount. The dotted line in FIG. 11 is the movement amount calculated based on the movement information acquired by the acceleration sensor 16. The movement amount at the end of measurement corresponds to the circumference of the measured object. In the present embodiment, the movement amount corresponds to the abdominal girth. The movement amount at the end of measurement is corrected so as to equal the abdominal girth actually measured in advance by a tape measure or other instrument. In greater detail, the movement amount at the end of measurement is offset by the correction amount ΔW in FIG. 11, and the inclination of the graph is corrected to match the movement amount offset by ΔW. The corrected data is indicated by a solid line. The controller 10 calculates the first contour of the object using the records that include the corrected, solid-line data.

Next, correction of the orientation and position of the calculated first contour is described. Upon setting the orientation of the smartphone 1 at the start of measurement to 0°, the axis of symmetry of the calculated first contour might be inclined. For example, in the case of the first contour, the user may wish to correct the inclination and display the contour with the abdomen or the back directly facing the y-axis direction in FIG. 10. On the coordinate axes of FIG. 10, the inclination may be corrected by rotating the first contour so that the width of the first contour in the x-axis direction or the width of the first contour in the y-axis direction is minimized or maximized.

If the position coordinates of the smartphone 1 at the start of measurement are at the xy origin in FIG. 10, the calculated first contour is displayed as being shifted from the center. The user may wish for the xy origin in FIG. 10 and the center of the first contour to coincide when the first contour is displayed. The center of the first contour may be considered the intersection of the widest center line of the first contour in the x-axis direction and the widest center line of the first contour in the y-axis direction. Furthermore, the center of a cross-section of the first contour may be moved to the xy origin of FIG. 10. The smartphone 1 may determine the intersection of the first contour and the y-axis (the intersection in the positive y-axis direction in the example in FIG. 10) to be the position of the user's umbilicus.

As described above, in a device according to the present embodiment, the contour of the object can be measured by a sensor built into the smartphone 1. The measured contour of the object is used as a wire frame for generating a three-dimensional image. The smartphone 1 is smaller than a measurement apparatus such as a CT apparatus. The smartphone 1 can also rapidly measure the contour of the object. Users of the smartphone 1 can measure data themselves, thereby simplifying measurement. The smartphone 1 can be carried easily, which is not true of CT apparatuses and the like. Since users of the smartphone 1 can measure data themselves, they can easily recognize day-to-day changes. The smartphone 1 also entails little risk of radiation exposure during measurement.

Figure 12:
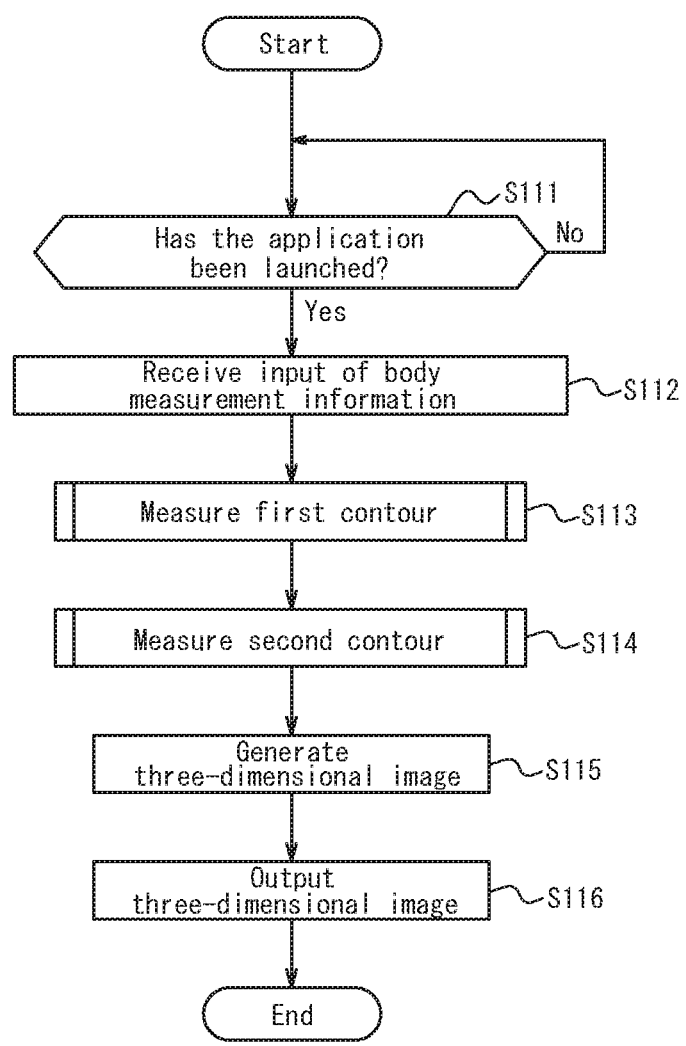
FIG. 12 is a flowchart for outputting a three-dimensional image according to the first embodiment.

Next, details of the method of generating a three-dimensional image with the smartphone 1 are described. FIG. 12 is a flowchart for generating a three-dimensional image according to the first embodiment.

In step S111, the user launches the measurement application 9Z.

Next, the user inputs body measurement information to the smartphone 1. The body measurement information may, for example, include any of height, sitting height, and abdominal girth. In step S112, the smartphone 1 receives input of the body measurement information based on user operation input. Step S112 may be omitted when, for example, the body measurement information has been inputted in advance and stored in the storage 9.

Next, in step S113, the smartphone 1 measures the first contour. In step S114, the smartphone 1 measures the second contour. Details of the method by which the smartphone 1 measures the first and second contours are as described with reference to FIG. 7 and the like.

In step S115, the smartphone 1 generates a three-dimensional image based on the measured first and second contours.

Figure 13:
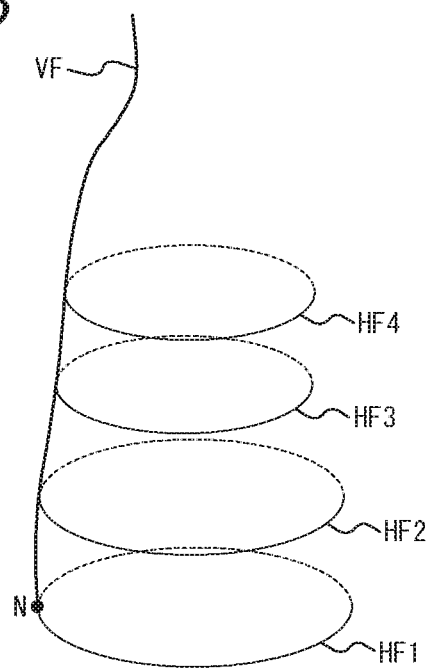
FIG. 13 illustrates an example of a three-dimensional image generated in the first embodiment.

FIG. 13 illustrates an example of a three-dimensional image generated in the first embodiment. Four first contours HF1, HF2, HF3, HF4 and one second contour VF are depicted in FIG. 13. The first contours HF1, HF2, HF3, HF4 and the second contour VF were generated as wire frame images. The smartphone 1 combines the wire frame images to generate a three-dimensional wire frame image as the three-dimensional image.

One first contour HF1 and the second contour VF include an umbilical portion N. In other words, in the example in FIG. 13, the first contour HF1 is a contour measured along the circumferential direction of the torso including the umbilicus, and the second contour VF is a contour measured along the midline of the torso. The first contours HF1, HF2, HF3, HF4 are contours the user measured sequentially while changing the height at which the smartphone 1 was placed against the object. The first contours HF1, HF2, HF3, HF4 were measured in this order from lowest to highest position.

As illustrated in FIG. 13, the controller 10 generates a three-dimensional image by crossing each of the first contours HF1, HF2, HF3, HF4 with the second contour VF. At this time, the controller 10 crosses the first contour HF1 and the second contour VF so that the umbilical portion N of the first contour HF1, which includes the umbilical portion N, coincides with the umbilical portion N of the second contour VF. The first contours HF2, HF3, HF4 that do not include the umbilical portion N are parallel to the first contour HF1 that includes the umbilical portion N and to each other. The four first contours HF1, HF2, HF3, HF4 are lined up in this order, i.e. the same order as when measured. A three-dimensional image such as the one in FIG. 13 is thereby generated.

Returning to FIG. 12, the smartphone 1 proceeds to step S116 and outputs the three-dimensional image generated in step S115. Examples of methods for outputting the three-dimensional image include displaying the image on the display 2A and transmitting the image to a server. For example, the smartphone 1 displays the three-dimensional image illustrated in FIG. 13 on the display 2A. Once output of the three-dimensional image is complete, the smartphone 1 ends the processing flow. The user who sees the displayed three-dimensional image can easily understand the shape of the abdomen visually.

Figure 14:
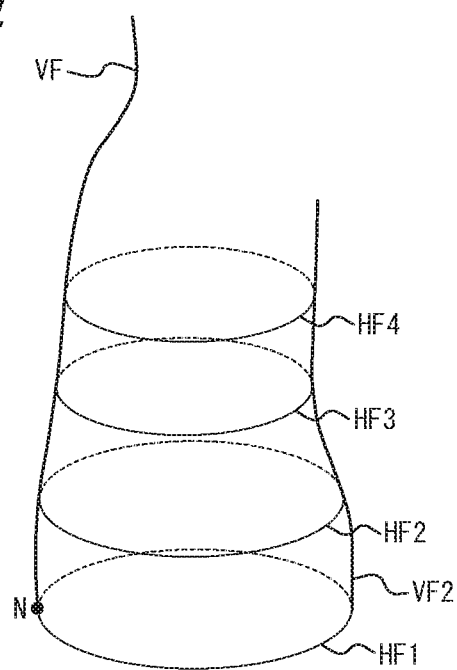
FIG. 14 illustrates another example of a three-dimensional image generated in the first embodiment.

When generating the three-dimensional image in step S115, the controller 10 may draw a curve VF2 connecting points on the back side of the first contours HF1, HF2, HF3, HF4, as in the example in FIG. 14, to generate a three-dimensional image that includes a virtual contour at the back side. The points on the back side may be points at positions opposite the positions where the first contours HF1, HF2, HF3, HF4 intersect the second contour VF. In this case, the smartphone 1 can display the three-dimensional image illustrated in FIG. 14 on the display 2A. Display of the three-dimensional image including the virtual contour at the back side allows the user to easily understand the shape of the abdomen visually.

Figure 15:
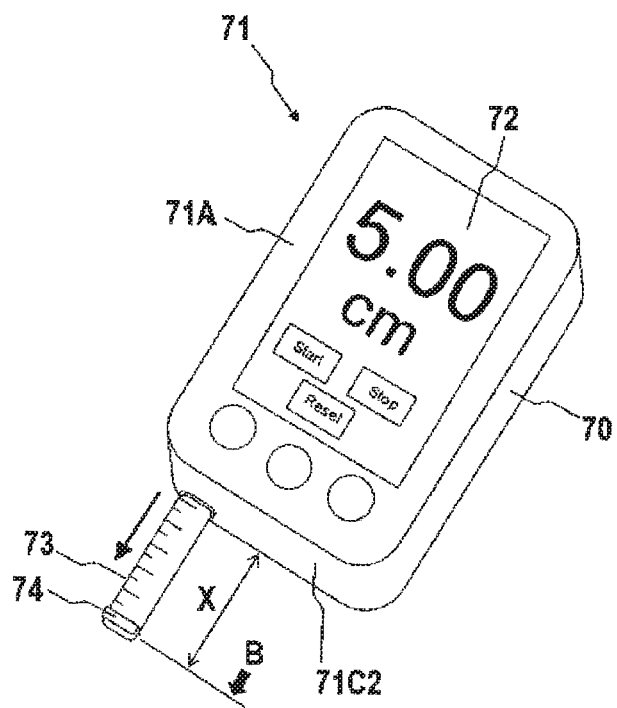
FIG. 15 schematically illustrates an electronic tape measure according to the first embodiment.

FIG. 15 schematically illustrates an electronic tape measure according to the first embodiment.

An electronic tape measure has a function to measure the length of extracted tape and acquire data. Hence, an electronic tape measure can acquire movement information like the acceleration sensor 16. The electronic tape measure may also be built into the smartphone 1.

An electronic tape measure 71 includes a housing 70. A touchscreen display 72 is provided on a front face 71A of the housing 70. A tape measure 73 is provided on the side face 71C2 of the housing 70. Measurement markings are inscribed on the tape measure 73. The tape measure 73 is normally wound up inside the housing 70. A stopper 74 is provided at the end of the tape measure 73. Before measurement, the stopper 74 is placed outside of the housing 70, and the B face of the stopper 74 is in contact with the side face 71C2. To measure a dimension of the object, the stopper 74 is pulled in the direction of the arrow in FIG. 15 to extract the tape measure 73 from the housing 70. At this time, the extracted amount X of the tape measure 73 with reference to the side face 71C2 is digitally displayed on the touchscreen display 72. The embodiment in FIG. 15 illustrates the case of X=5.00 cm.

In the case of the electronic tape measure 71 being used as the second sensor of the smartphone 1 in the present embodiment, the measurement procedure and the calculation of the contour of the object conform to the description of FIGS. 5 through 10. The measurement procedure when the electronic tape measure 71 is used is described below. At the start of measurement in step S102, the housing 70 is placed against the surface of the abdomen. In step S103, the user moves the housing 70 along the surface at the A-A position of the abdomen 60 around the abdomen 60 once while holding the stopper 74 at the measurement start position. Measurement ends when the side face 71C2 and the B face of the stopper 74 coincide (step S104).

When the acceleration sensor 16 is used as the second sensor, the acceleration is acquired as the movement information. By contrast, when the electronic tape measure 71 is used as the second sensor, the length is acquired directly as the movement information. Use of the electronic tape measure 71 as the second sensor thus allows more accurate measurement of the abdominal girth.

The smartphone 1 according to the present embodiment may associate the three-dimensional image generated in step S115 with the time at which the three-dimensional image was generated and store the associated three-dimensional image and time in the storage 9. For example, the smartphone 1 acquires information related to the time at which the three-dimensional image was generated ("time information"). The smartphone 1 acquires the time information using a clock function, such as a real-time clock (RTC). The time information is not necessarily acquired when the three-dimensional image is generated in step S115. The time information may, for example, be acquired at any timing related to generation of the three-dimensional image, such as after the application is launched in step S111.

In addition to the three-dimensional image generated by the smartphone 1 and the time information thereof, other information that could be related to the shape of the abdomen may be stored in the storage 9. An example of information stored by the storage 9 is now described.

For example, the storage 9 of the smartphone 1 may store information related to food or drink consumed by the user in association with the time at which the food or drink was consumed. The information related to food or drink may, for example, include at least one of the type of food or drink, the amount, and the number of calories. The information related to food or drink may, for example, include at least one of the name of the food or drink and the raw materials and ingredients (such as nutrients) included in the food or drink. Food or drink in this context may include any of general food items, health food, and medicine.

The smartphone 1 can acquire information related to food or drink by various methods. For example, the smartphone 1 can acquire information related to food or drink by receiving input from the user to the touchscreen 2B and/or the buttons 3. In this case, the user uses the touchscreen 2B and/or the buttons 3 to input information related to food or drink directly to the smartphone 1. The user inputs information related to food or drink when consuming the food or drink, for example. The controller 10 of the smartphone 1 stores the time at which the information related to food or drink was inputted in the storage 9 in association with the information related to food or drink.

The smartphone 1 may acquire information related to food or drink based on information included in the food or drink package, for example. The information included in the food or drink package includes a barcode, or Japanese article number (JAN), for example. When a barcode is listed on the food or drink package, the user photographs the barcode using the camera 13 of the smartphone 1. The controller 10 of the smartphone 1 reads the photographed barcode and stores information related to the product associated with the barcode in the storage 9 as the information related to food or drink. At this time, the controller 10 may acquire the information related to the product associated with the barcode by communicating with an external information processing apparatus, for example. The user reads the barcode using the smartphone 1 when consuming the food or drink, for example. The controller 10 of the smartphone 1 stores the time at which the barcode was read in the storage 9 in association with the information related to food or drink. When codes other than the barcode (for example, a one-dimensional code or two-dimensional code) are included on the food or drink package, the smartphone 1 may acquire the information related to food or drink by reading the other codes.

The information related to food or drink includes a radio frequency identifier (RFID), for example. Suppose that an RFID tag with information related to food or drink is provided in the food or drink package, and the smartphone 1 is an electronic device supporting RFID. In this case, the user causes the smartphone 1 to acquire the information related to food or drink from the RFID tag provided in the food or drink package. The controller 10 of the smartphone 1 stores the acquired information related to food or drink in the storage 9. The controller 10 of the smartphone 1 stores the time at which the information related to food or drink was acquired by RFID communication in the storage 9 in association with the information related to food or drink.

The information related to food or drink includes information related to nutritional information listed on a package, for example. When information related to nutritional information is listed on a food or drink package, for example, the user photographs the nutritional information column on the package using the camera 13 of the smartphone 1. The controller 10 of the smartphone 1 reads the photographed nutritional information column and stores the information listed as nutritional information (in this case, the number of calories, the nutrients included in the food product and the amount thereof, and the like) in the storage 9 as the information related to food or drink. At this time, the controller 10 may communicate with an external information processing apparatus, for example, and transmit the captured image to the external information processing apparatus. In this case, the external information processing apparatus reads the photographed nutritional information column and transmits the information listed as nutritional information to the smartphone 1. The smartphone 1 stores the acquired information in the storage 9 as information related to food or drink. The controller 10 of the smartphone 1 stores the time at which the nutritional information column was photographed in the storage 9 in association with the information related to food or drink.

The information related to food or drink may be estimated based on an image of the food or drink. For example, the user uses the camera 13 of the smartphone 1 to photograph an image of the food or drink before consumption. The controller 10 estimates the information related to food or drink by analyzing the photographed image. The controller 10 can perform image analysis to estimate the amount of the food or drink based on the volume of the food or drink, for example. The controller 10 can, for example, perform image analysis to estimate the nutrients included in the food or drink based on the color of the food or drink. The color of the ingredients in the food or drink does not necessarily correspond to the nutrients included in the ingredients. The nutrients can be estimated, however, from the color of the ingredients. The controller 10 may estimate the calories in the food or drink based on the photographed image. The controller 10 stores the estimated information in the storage 9 as the information related to food or drink. The controller 10 stores the time at which the image of the food or drink was captured in the storage 9 in association with the information related to food or drink.

Estimation of the information related to food or drink based on the photographed image of the food or drink is not necessarily made by the controller 10 of the smartphone 1. For example, the controller 10 of the smartphone 1 may transmit the photographed image of the food or drink to an external information processing apparatus. The external information processing apparatus estimates the information related to food or drink based on the image of the food or drink. The external information processing apparatus then transmits the estimated information related to food or drink to the smartphone 1. The smartphone 1 stores the information related to food or drink acquired from the external information processing apparatus in the storage 9.

In addition to the image of the food or drink before consumption, the user may also capture an image of the food or drink after consumption using the camera 13 of the smartphone 1. In this case, the controller 10 or the external information processing apparatus can estimate the content of the user's leftover food or drink based on the image of the food or drink after consumption. The controller 10 or the external information processing apparatus can therefore more easily estimate the information related to food or drink for the food or drink actually consumed by the user.

The storage 9 of the smartphone 1 may store information related to the user's physical activity in association with the time at which the physical activity was performed. In the present disclosure, the information related to physical activity refers to activity performed as part of the user's life. The information related to physical activity may, for example, include information related to exercise and information related to sleep. The information related to exercise may, for example, include at least one of the amount of exercise and calories burned. In the present disclosure, the amount of exercise may include the content and duration of exercise. The information related to sleep may include the hours of sleep.

The smartphone 1 can acquire information related to exercise by various methods. For example, the smartphone 1 can acquire information related to exercise by receiving input from the user to the touchscreen 2B and/or the buttons 3. In this case, the user uses the touchscreen 2B and/or the buttons 3 to input information related to exercise directly to the smartphone 1. The user may, for example, input information related to exercise before or after performing exercise. Based on user input, the controller 10 of the smartphone 1 stores the time at which the user performed exercise in the storage 9 in association with the information related to exercise.

The smartphone 1 may estimate the information related to exercise based on information acquired by a sensor provided in the electronic device. For example, when the user is wearing the smartphone 1 while exercising, the controller 10 of the smartphone 1 estimates the information related to exercise, such as the intensity and duration of exercise, based on the magnitude of the user's body movements detected by the motion sensor 15. The controller 10 judges that the user is exercising when, for example, the magnitude of body movements exceeds a predetermined body movement threshold. The controller 10 estimates the duration of exercise by the user as the length of time that the magnitude of body movements continuously exceeds the predetermined body movement threshold. The controller 10 can estimate the starting time of exercise as the time when the magnitude of body movements exceeds the threshold and the ending time as the time when the magnitude of body movements falls below the threshold. The controller 10 may set a plurality of predetermined body movement thresholds and estimate the starting time and ending time of exercise corresponding to exercise at a plurality of intensity levels. The controller 10 may count the number of steps based on the user's body movements and calculate the calories burned from the number of steps.

When the smartphone 1 includes a sensor capable of detecting biological information, such as the user's pulse or body temperature, the controller 10 may estimate the information related to exercise based on the biological information. A person's pulse increases during exercise, and the body temperature rises. Predetermined exercise judgment thresholds may be set in advance for the pulse and body temperature to judge whether the user is exercising. The controller 10 can estimate the starting time of exercise as the time at which the pulse and body temperature exceed the predetermined exercise judgment thresholds. The controller 10 can also estimate the user's exercise intensity based on changes in the pulse and body temperature.

After estimating the information related to exercise, the controller 10 stores the time at which the user performed exercise in the storage 9 in association with the estimated information related to exercise. The time at which the user performed exercise may be either or both of the exercise starting time and the exercise ending time.

The information related to exercise is not necessarily estimated by the controller 10 of the smartphone 1. For example, an information processing apparatus external to the smartphone 1 may estimate the information related to exercise and transmit the estimated information related to exercise to the smartphone 1. The controller 10 of the smartphone 1 stores the information related to exercise acquired from the external information processing apparatus in the storage 9.

The information used to estimate the information related to exercise is not necessarily acquired by the smartphone 1. For example, information from the user may be acquired by a dedicated electronic device that differs from the smartphone 1 and includes a motion sensor capable of detecting the user's body movements or a biological sensor capable of acquiring biological information of the user. In this case, the information acquired by the dedicated electronic device may be transmitted to the smartphone 1 or the external information processing apparatus, and information related to exercise may be estimated on the smartphone 1 or the external information processing apparatus.

The smartphone 1 can acquire information related to sleep by various methods. For example, the smartphone 1 can acquire the information related to sleep by receiving input from the user to the touchscreen 2B and/or the buttons 3. In this case, the user uses the touchscreen 2B and/or the buttons 3 to input the information related to sleep directly to the smartphone 1. The user can input the information related to sleep by operating the smartphone 1 before going to bed or after getting up, for example. Based on user input, the controller 10 of the smartphone 1 stores the time related to the user's sleep (such as the time the user falls asleep) in the storage 9 in association with the information related to sleep.

The smartphone 1 may infer the information related to sleep based on information acquired by a sensor provided in the electronic device. For example, when the user is wearing the smartphone 1 while sleeping, the controller 10 of the smartphone 1 infers the information related to sleep based on the user's body movements detected by the motion sensor 15. The estimation by the controller 10 of information related to sleep is now described in detail. It is known that people repeatedly experience two sleeping states, REM sleep and non-REM sleep, over a nearly constant cycle while sleeping. People are more likely to turn over during REM sleep and less likely to turn over during non-REM sleep. The controller 10 uses these tendencies to infer the user's sleep state based on body movements caused by the user turning over. In other words, the controller 10 infers that the time period when body movements are detected in a predetermined cycle is non-REM sleep and infers that the time period when body movements are not detected in a predetermined cycle is REM sleep. The two sleep states are repeated over a nearly constant cycle. Therefore, after determining the cycle of the two sleep states, the controller 10 can calculate backwards to estimate the time at which the user actually fell asleep based on the time periods of the two sleep states.

When the smartphone 1 includes a sensor capable of detecting biological information, such as the user's pulse or body temperature, the controller 10 may estimate the information related to exercise based on the biological information. When people sleep, their pulse lowers, and their body temperature falls. The controller 10 can set predetermined sleep judgment thresholds in advance for the pulse and body temperature and estimate the actual time at which the user falls asleep as the time when the pulse and body temperature fall below the predetermined sleep judgment thresholds.

Like the information related to exercise, the information related to sleep may also be estimated by an external information processing apparatus. Furthermore, like the information related to exercise, the information related to sleep may also be estimated based on information acquired by a dedicated electronic device.

FIG. 16 illustrates example data stored in the storage 9 of the smartphone 1. As illustrated in FIG. 16, various information is stored in the storage 9 in association with time (date and time). For example, the three-dimensional image generated by the smartphone 1 and information related thereto are stored in the storage 9 in association with time. The information related to the three-dimensional image may, for example, include information related to the first contour and the second contour. The information related to the three-dimensional image may, for example, be information related to the first contour that includes the umbilical portion N among the plurality of first contours. The information related to the three-dimensional image may include the abdominal girth, the visceral fat area, the subcutaneous fat area, the vertical/horizontal length, and the aspect ratio as the information related to the first contour that includes the umbilical portion N, as illustrated in FIG. 16.

The abdominal girth is calculated by the method described with reference to FIG. 7. The abdominal girth may be inputted by the user.

The visceral fat area and the subcutaneous fat area are, for example, estimated based on the calculated first contour that includes the umbilical portion N. The method by which the smartphone 1 estimates the visceral fat area and the subcutaneous fat area is now described. For example, the storage 9 stores estimation formulas, derived in advance, for the visceral fat area and the subcutaneous fat area. The controller 10 extracts characteristic coefficients of the first contour of the object calculated as described above. The controller 10 reads the estimation formulas, stored in the storage 9, for the visceral fat area and the subcutaneous fat area and estimates the visceral fat area and the subcutaneous fat area using the extracted characteristic coefficients of the contour.

Specifically, the smartphone 1 extracts the characteristic coefficients of the first contour after correcting the first contour, for example. Methods of extracting the characteristics of a curved shape include a method of calculating a curvature function. In the present embodiment, however, a method using Fourier analysis is described. By subjecting one circumference of the first contour to Fourier analysis, the controller 10 can seek the Fourier coefficients. As is well known, the Fourier coefficients of different orders that are sought when the curve is subjected to Fourier analysis are used to indicate the characteristics of the shape. The orders of Fourier coefficients that are extracted as characteristic coefficients are determined when deriving estimation formulas, which are described below in detail. In the present embodiment, the Fourier coefficients $Sa_1$, $Sa_2$, $Sa_3$, $Sa_4$ that affect the visceral fat area are extracted as characteristic coefficients of the visceral fat. Similarly, the Fourier coefficients $Sb_1$, $Sb_2$, $Sb_3$, $Sb_4$ that affect the subcutaneous fat area are extracted as characteristic coefficients of the subcutaneous fat. If the independent variables of each estimation formula are taken to be the principle components when the estimation formula is derived, then the principle components may be extracted as the characteristic coefficients.

The smartphone 1 estimates the user's visceral fat area and subcutaneous fat area by substituting the extracted characteristic coefficients $Sa_1$ to $Sa_4$ and $Sb_1$ to $Sb_4$ into the visceral fat area estimation formula and the subcutaneous fat area estimation formula calculated in advance. Examples of the visceral fat area estimation formula and the subcutaneous fat area estimation formula are illustrated in Equations 1 and 2.

$$A = -483.8 + 46.2 \times Sa_1 - 13.6 \times Sa_2 + 36.8 \times Sa_3 + 43.2 \times Sa_4 \quad \text{[Equation 1]}$$

$$B = -280.0 + 41.6 \times Sb_1 - 24.9 \times Sb_2 + 16.6 \times Sb_3 - 40.0 \times Sb_4 \quad \text{[Equation 2]}$$

The method of deriving the visceral fat area estimation formula and the subcutaneous fat area estimation formula is now described. FIG. 17 is a flowchart for deriving the visceral fat area estimation formula and the subcutaneous fat area estimation formula. The procedure for deriving Equation 1 and Equation 2 is described with reference to FIG. 17. These estimation formulas need not be derived on the smartphone 1 and may be calculated in advance on another apparatus, such as a computer. The derived estimation formulas are read into the application in advance. Therefore, the user need not derive or change the estimation formulas directly.

In step S121, the author derives an estimation formula. In step S122, the author inputs sample data, acquired in advance, for a predetermined number of people into the computer. The sample data is acquired from a predetermined number of sample subjects. The sample data for one subject at least includes the visceral fat area and subcutaneous fat area obtained by CT, the abdominal girth measured by a tape measure or other instrument, orientation information acquired by the smartphone 1, and movement information. To improve accuracy of the estimation formulas, the predetermined number of sample subjects may be a statistically significant number and may be a group having a similar distribution to the visceral fat distribution of subjects for metabolic syndrome (MS) diagnosis.

Next, the computer calculates the first contour that includes the umbilical portion N from the inputted abdominal girth, orientation information, and movement information (step S123). Furthermore, the computer corrects the calculated first contour (step S124).

Next, the computer performs Fourier analysis on the curve of the calculated, corrected first contour (step S125). By subjection of the curve of the first contour to Fourier analysis, a plurality of Fourier coefficients can be sought. As is well known, the Fourier coefficients of different orders that are obtained when the curve is subjected to Fourier analysis are used to represent the characteristics of the shape. In the present embodiment, the sample data for a predetermined number of people is subjected to Fourier analysis to seek the x-axis, y-axis, and $1^{st}$ to $k^{th}$ order Fourier coefficients (where k is any integer). Furthermore, the Fourier coefficients may be subjected to well-known principle component analysis to reduce the number of dimensions. As the analysis method for principle component analysis, a common component may be sought for multivariate data (in the present embodiment, a plurality of Fourier coefficients), and a type of composite variable (principle component) may be derived. The characteristics of the curve can thus be represented with even fewer variables.

Next, regression analysis is performed with the plurality of Fourier coefficients (or principle components) sought in step S125 and the visceral fat area inputted in advance (step S126). Regression analysis refers to a statistical method for examining and clarifying the relationship between a numerical value representing a result and a numerical value representing a cause. With the Fourier coefficients (or principle components) as independent variables and the visceral fat area obtained by CT as a dependent variable, regression analysis is performed using the data of a predetermined number of sample subjects to derive the visceral fat area estimation formula (step S127). Similar calculations are made for the subcutaneous fat area to derive the subcutaneous fat area estimation formula.

Equation 1 and Equation 2 above are examples of the estimation formulas derived in this way. The independent variables Sa1, Sa2, Sa3, Sa4, and Sb1, Sb2, Sb3, Sb4 in Equation 1 and Equation 2 are the characteristic coefficients for estimating the user's visceral fat area and subcutaneous fat area. A portion or all of the characteristic coefficients Sa1 to Sa4 of the visceral fat area estimation formula and the characteristic coefficients Sb1 to Sb4 of the subcutaneous fat area may be the same Fourier coefficients. In this way, the estimation formulas for visceral fat area and subcutaneous fat area can be derived by the above-described statistical means (such as principle component analysis and regression analysis).

The estimation formulas are derived in step S126 by performing regression analysis for the visceral fat area and the subcutaneous fat area. An estimation formula can also be derived with a similar method for the length of the first contour (the circumference of an abdominal cross-section). In other words, regression analysis is performed with the plurality of Fourier coefficients (or principle components) sought in step S125 and the abdominal girth inputted in advance. With the Fourier coefficients (or principle components) as independent variables and the abdominal girth measured by a tape measure or other instrument as the dependent variable, regression analysis can be performed using the data of a predetermined number of sample subjects to derive the estimation formula for the first contour length.

The smartphone 1 according to the present embodiment can use the above-described method to easily measure the first contour accurately. The smartphone 1 can therefore quickly estimate the visceral fat area and the subcutaneous fat area accurately.

Referring again to FIG. 16, the information related to the first contour may, for example, include the vertical and horizontal length (width) and the aspect ratio. The vertical and horizontal length and the aspect ratio are, for example, estimated based on the calculated first contour. The horizontal length of the first contour is the width of the first contour in a front view of the person. The horizontal length of the first contour is the width of the first contour in the x-axis direction in FIG. 10. The vertical length of the first contour is the width of the first contour in a side view of the person and is the width in the direction orthogonal to the horizontal width of the first contour. The vertical length of the first contour is the width of the first contour in the y-axis direction in FIG. 10. The aspect ratio of the first contour is the ratio of the vertical length to the horizontal length of the first contour.

Figure 18A:
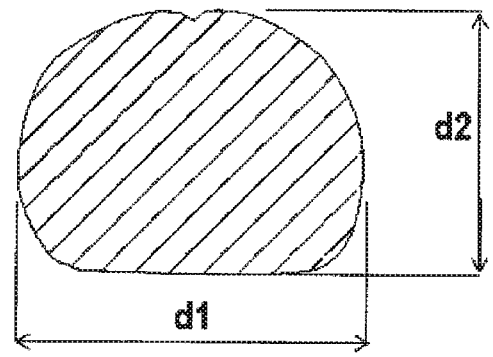
FIGS. 18A, 18B, and 18C are schematic diagrams illustrating example classifications of a first contour in the first embodiment.
Figure 18B:
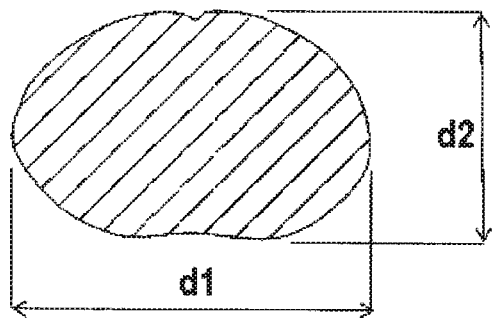
Figure 18C:
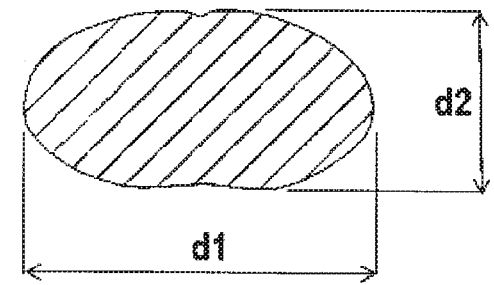

The classification of the first contour including the umbilicus portion N may be stored in the smartphone 1 in advance. FIGS. 18A, 18B, and 18C are conceptual diagrams illustrating example classifications of the first contour. The classifications of the first contour illustrated in FIGS. 18A, 18B, and 18C are A visceral obesity, B subcutaneous fat, and C average. The user is classified into one of A to C by the aspect ratio (d2/d1 in FIG. 18) of the measured first contour that includes the umbilicus portion N. For example, an aspect ratio of 0.8 or more is classified as A visceral obesity, 0.6 or more to less than 0.8 as B subcutaneous fat, and less than 0.6 as C average. In this case, a [classification] step may be added after step S105 in the flowchart in FIG. 7. The user can receive the result of classification and/or advice in accordance with the classification. The classification may be stored in the storage 9 along with the vertical and horizontal lengths of the first contour and the aspect ratio.

The user may, for example, measure the contour of the object with the smartphone 1 regularly and continuously. The contour of the object may, for example, be measured every day, once a week, or once a month. The contour of the object may be measured in the same time slot of the day. For example, the contour of the object may be measured before a 7:00 am meal. Data can be acquired under the same conditions more easily when the contour of the object is measured in the same time slot.

Referring again to FIG. 16, information related to food or drink and information related to physical activity are stored in the storage 9 in association with the time, for example.

The information related to food or drink may include a food menu, the user's calories consumed, beverages, health food, and medicine. The name of the food or drink and the amount thereof, for example, are stored in the storage 9 as the information related to food or drink.

The information related to physical activity may include the calories burned by the user and the hours of sleep.

The smartphone 1 can acquire the information related to food or drink and the information related to physical activity by the above-described methods, for example.

The smartphone 1 can display two three-dimensional images stored in the storage 9 on the display 2A. The smartphone 1 may display three-dimensional images generated at different times side-by-side. In other words, the smartphone 1 may display a first three-dimensional image measured at a first time and a second three-dimensional image measured at a second time side-by-side.

Figure 19:
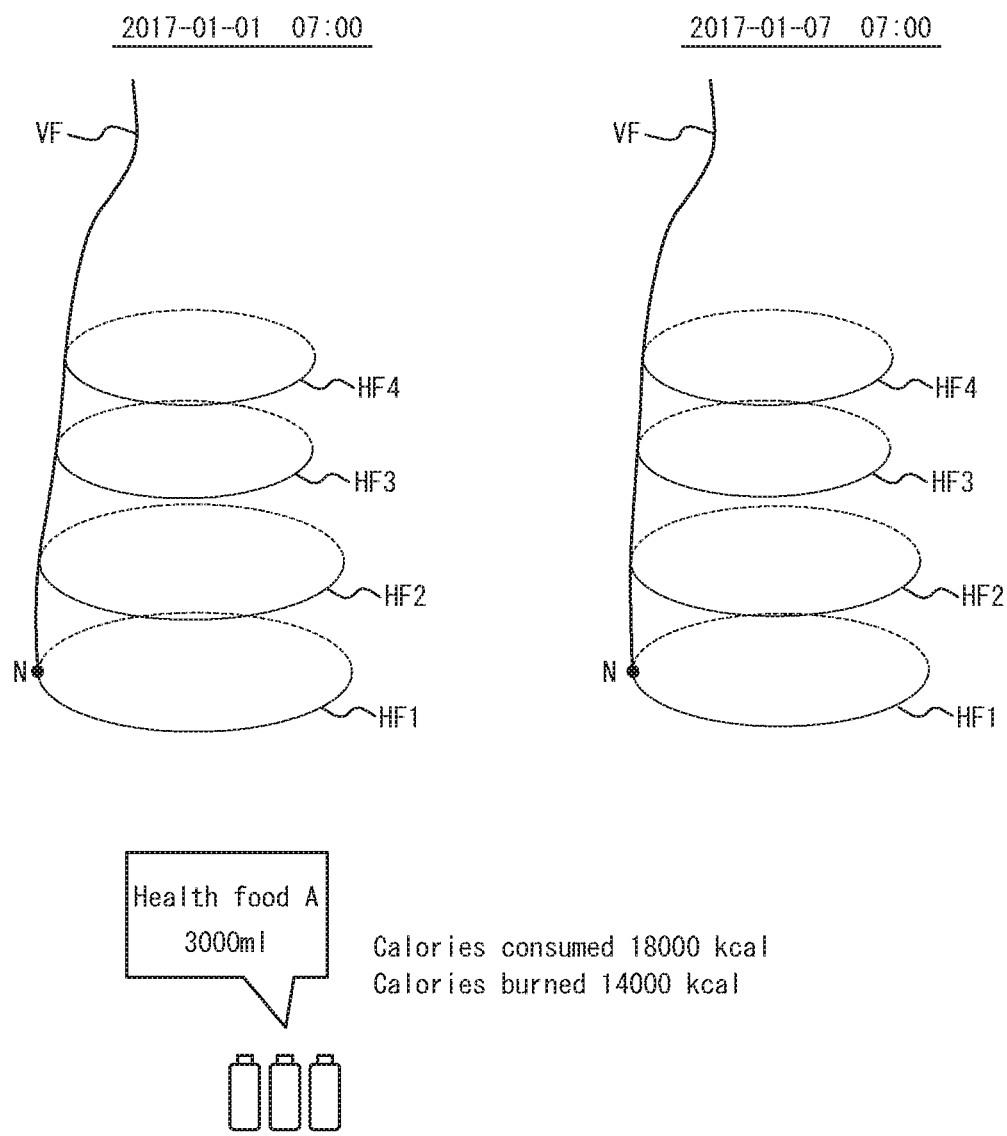
FIG. 19 illustrates an example display by the smartphone according to the first embodiment.

FIG. 19 illustrates an example display by the smartphone 1. In the example in FIG. 19, the first three-dimensional image was generated at a first time of 7:00 am on Jan. 1, 2017, and the second three-dimensional image was generated at a second time of 7:00 am on Jan. 7, 2017. The user can visually understand the change over time in the shape of the object through the side-by-side display of two three-dimensional images.

The two three-dimensional images displayed side-by-side may, for example, be determined automatically by the controller 10. For example, when the controller 10 generates a three-dimensional image, the controller 10 may determine to display the generated three-dimensional image and a three-dimensional image generated at a predetermined earlier time (such as the previous day, week, or month). The two three-dimensional images displayed side-by-side may, for example, be determined based on user selection. In this case, the user can learn the change in the shape of the object between two desired time periods (dates and times).

The number of three-dimensional images that the smartphone 1 displays side-by-side is not necessarily two. The smartphone 1 may display three or more three-dimensional images side-by-side. In this case as well, the user can understand the change over time in the shape of the object.

In addition to the two three-dimensional images, the smartphone 1 may display information related to food or drink and/or information related to physical activity occurring between when the two three-dimensional images were generated (between the first time and the second time), as illustrated in FIG. 19. The total number of calories consumed and the total number of calories burned by the user between the times at which the two three-dimensional images were generated are displayed in the example in FIG. 19. The name and amount of the health food consumed by the user between the times at which the two three-dimensional images were measured are displayed in the example in FIG. 19. The information related to food and drink and information related to physical activity that are displayed are not limited to the example in FIG. 19. For example, a portion or all of the data stored in the storage 9, an example of which is illustrated in FIG. 16, may be displayed together with the two three-dimensional images. The display of the information related to food or drink and/or information related to physical activity occurring between when the two three-dimensional images were generated makes it easier for the user to guess the relationship that food or drink and/or physical activity has with the change in shape of the object. For example, when information related to food and drink is displayed, the user can easily understand how the shape of the object changed in response to certain eating habits.

Figure 20:
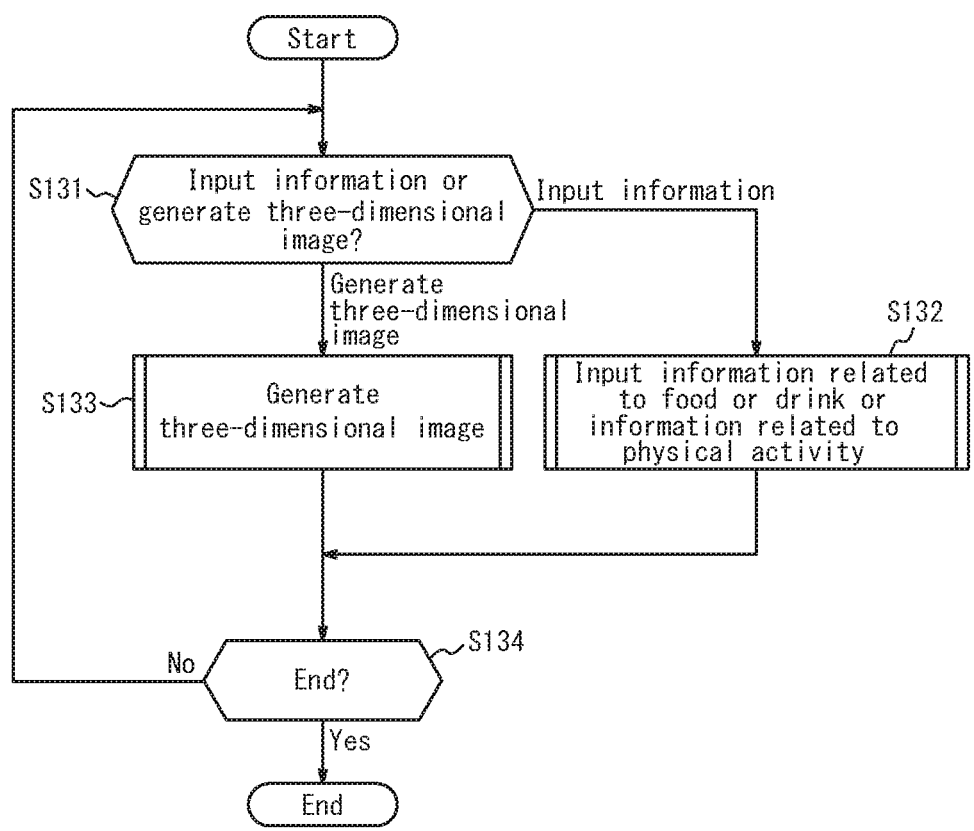
FIG. 20 is a flowchart of the entire processing by the smartphone according to the first embodiment.

FIG. 20 is a flowchart of the entire processing executed by the smartphone 1 according to the present embodiment. In step S131, the smartphone 1 determines whether to input information or to generate a three-dimensional image based on operation input from the user.

When the smartphone 1 determines in step S131 to input information, the smartphone 1 receives input of information related to food or drink or information related to physical activity based on user operation input in step S132. Details on the input of information related to food or drink or information related to physical activity are as described above. The input of information may, for example, include capturing an image of food or drink or receiving input of calories consumed.

After the smartphone 1 receives input of information in step S132, the smartphone 1 judges in step S134 whether the user has inputted an instruction to end processing. When the smartphone 1 judges that an instruction to end processing has been inputted, the smartphone 1 ends the processing flow in FIG. 20. Conversely, when the smartphone 1 judges that an instruction to end processing has not been inputted (for example, when an instruction to continue processing has been inputted), the smartphone 1 proceeds to step S131.

When the smartphone 1 determines in step S131 to measure the contour, the smartphone 1 generates a three-dimensional image in step S133. Details of step S133 are as described with reference to FIG. 7. The smartphone 1 may display the measured contour after measuring the contour.

After the smartphone 1 measures the contour in step S133, the smartphone 1 judges in step S134 whether the user has inputted an instruction to end processing. When the smartphone 1 judges that an instruction to end processing has been inputted, the smartphone 1 ends the processing flow in FIG. 20. Conversely, when the smartphone 1 judges that an instruction to end processing has not been inputted (for example, when an instruction to continue processing has been inputted), the smartphone 1 proceeds to step S131.

Second Embodiment

Figure 21:
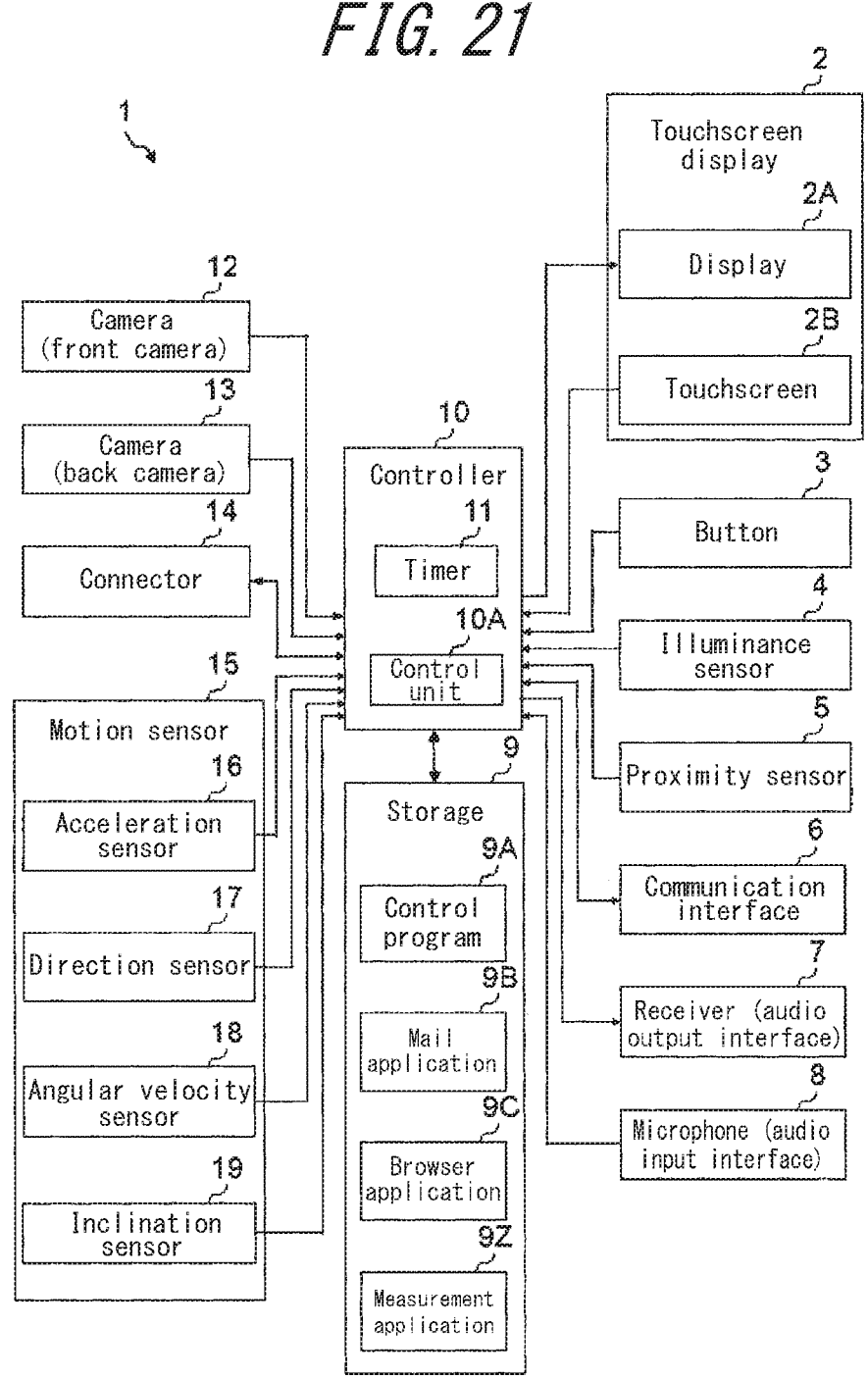
FIG. 21 is a schematic block diagram illustrating the functions of a smartphone according to a second embodiment.

FIG. 21 is a block diagram illustrating the configuration of a smartphone 1 according to the second embodiment.

In the present embodiment, a timer 11 and a control unit 10A are included in a controller 10. The timer 11 is a device for obtaining movement information of the smartphone 1. The timer 11 receives an instruction for a timer operation from the control unit 10A and outputs a clock signal. The direction sensor 17 acquires orientation information multiple times in accordance with the clock signal outputted from the timer 11. The orientation information acquired in accordance with the clock signal is temporarily stored inside the smartphone 1 along with clock information. Clock information refers to information indicating the time at which the orientation information was acquired. For example, the clock information may be a record number indicating the order of acquisition when using a clock signal with a constant period. The clock information may also be the time of acquisition of the orientation information. In the present embodiment, the timer 11 is included in the controller 10. A timer circuit that is a functional component of the controller 10 may be used as the timer 11. The present disclosure is not limited to this example. As described above with reference to FIG. 4, the timer 11 may be provided externally to the controller 10.

The control unit 10A estimates the movement information of the smartphone 1 from the clock information. The movement information of the smartphone 1 is related to the movement amount of the smartphone 1. In the present embodiment, the movement information is the movement amount. The control unit 10A calculates a contour of an object based on the movement information and generates a three-dimensional image based on the contour. The differences from the first embodiment are described below, with a description of common features being omitted.

Figure 22:
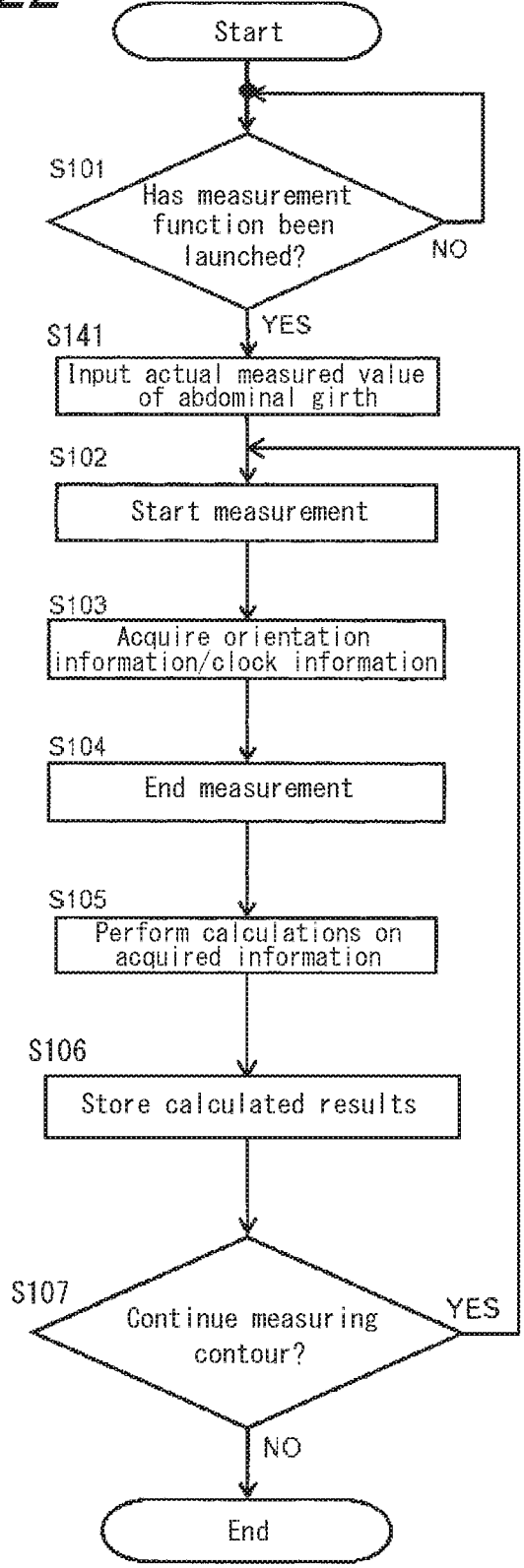
FIG. 22 is a flowchart for measuring the contour of an object according to the second embodiment.

FIG. 22 is a flowchart for measuring the contour of an object according to the second embodiment.

In step S101, the user activates the measurement function in the measurement application 9Z. After activating the measurement function in the measurement application 9Z, the user inputs the actual measured value of the abdominal girth, as measured in advance with a tape measure or other instrument, into the smartphone 1 (step S141). Alternatively, the smartphone 1 may read the actual measured value of the abdominal girth from user information stored in advance in the storage 9. The actual measured value of the abdominal girth need not be inputted before the start of measurement (step S102) and may instead be inputted after measurement is complete (step S104).

Next, measurement begins in step S102. At the start of measurement, the smartphone 1 is placed against the surface of the abdomen 60 at any position where the contour of the object is to be measured. For example, to measure the first contour, the smartphone 1 is placed against the surface of the abdomen 60 at the height of the user's umbilicus (the position indicated by line A-A in FIG. 5). The measurement start position may be anywhere along the abdominal A-A position. To start measurement, the user performs a preset start action on the smartphone 1. In step S103, the user moves the smartphone 1 along the surface at the A-A position of the abdomen 60. The user moves the smartphone 1 at constant speed while keeping the smartphone 1 against the surface of the abdomen 60. A support tool that facilitates movement of the smartphone 1 may be employed so that the user can move the smartphone 1 at constant speed. A supporting sound may be outputted at constant speed from the smartphone 1 to guide the operation.

In step S103, the smartphone 1 acquires orientation information with the direction sensor 17 under pre-programmed conditions. The orientation information is acquired multiple times in accordance with the clock signal outputted from the timer 11. The orientation information acquired in accordance with the clock signal is stored in the smartphone 1 along with the clock information. This measurement is continuously made from the start of step S102 until the end of step S104.

The user moves the smartphone 1 around the abdomen 60 once or more at constant speed while keeping the smartphone 1 against the surface of the abdomen 60. Subsequently, the user performs a preset end action on the smartphone 1 and ends measurement (step S104). Alternatively, the smartphone 1 may end measurement automatically, without user operation, by recognizing a complete circumference when the orientation information acquired by the direction sensor 17 of the smartphone 1 matches the orientation information at the start of measurement. The smartphone 1 may also end measurement automatically, without user operation, by recognizing a complete circumference when the orientation information acquired by the direction sensor 17 of the smartphone 1 changes by 360° from the orientation information at the start of measurement. In the case of automatic recognition, the user need not perform the end action, thereby simplifying measurement.

In step S105, the control unit 10A estimates the movement amount, which is the movement information of the smartphone 1, by the actual measured value of the user's abdominal girth and the clock information acquired in step S103. The circumferential movement amount of the smartphone 1 once around the user's abdominal girth is equivalent to the actual measured value of the abdominal girth inputted in step S141, and the smartphone 1 is considered to move at a constant speed. Therefore, the movement amount can be calculated as the movement information of the smartphone 1. The control unit 10A calculates the contour of the object based on the acquired orientation information and the calculated movement information.

In step S106, the smartphone 1 stores the results of the calculations performed in step S105 in the storage 9.

In step S107, the smartphone 1 judges whether to continue measuring the contour based on user operation input. When contour measurement is to be continued (step S107: YES), the smartphone 1 proceeds to step S102. In this case, the user can measure the first contour by placing the smartphone 1 against the abdomen 60 at a different height and moving the smartphone 1 in the first direction. After measuring the first contour at the height of the umbilicus, the user can measure the first contour at a position that is a predetermined distance higher than the umbilicus and then repeat the process to measure a plurality of first contours at different heights.

When contour measurement is not to be continued (step S107: NO), the smartphone 1 ends the processing flow. The other operations not described in detail in the flowchart of the present embodiment conform to the operations in FIG. 7.

FIG. 23 is an example record formed by acquired information according to the second embodiment.

The record number at the start of measurement is R0, and the record number at the end of measurement is Rn. In each record, orientation information and movement information corresponding to time are stored as a pair. The movement information is the movement amount estimated from the record number (or the time), which is clock information. The actual measured value of the user's abdominal girth is stored as the movement information of record number Rn. The time intervals between records are equal intervals, and the smartphone 1 is considered to move at a constant speed. Therefore, the interval between each movement amount, which is movement information, is also an equal interval. Records acquired in this way are displayed as a diagram indicating the first contour.

The first contour can be calculated by plotting the xy coordinates of the acquired records R0 to Rn in order in accordance with orientation and movement amount. In the present embodiment, each plotted point is at an equal interval in the calculated first contour illustrated in FIG. 10. When movement of the smartphone 1 is at a constant speed at the time of measurement, the calculated first contour has a nearly symmetrical shape about the y-axis. When movement of the smartphone 1 is not at a constant speed at the time of measurement, the calculated first contour has a non-symmetrical, irregular shape about the y-axis. When the shape of the calculated first contour is highly non-symmetrical, a message encouraging the user to measure again at constant speed may be displayed on the smartphone 1. The judgment of the magnitude of non-symmetry may be made based on the difference in the number of plotted points in the two regions separated by the y-axis in FIG. 10. For example, when the difference in the number of plotted points is other than ±10%, the first contour may be judged to be highly non-symmetrical. The method for judging the degree of non-symmetry is not limited to this example. For example, areas surrounded by the first contour may be calculated and compared to judge the degree of non-symmetry. The standard for judgment may be set as necessary.

The second contour may be measured in the same way.

In the present embodiment, use of the timer 11 as the device for obtaining movement information of the electronic device allows the movement information to be acquired without use of the second sensor.

Therefore, the number of components can be further reduced in the smartphone 1 of the present embodiment. Furthermore, the smartphone 1 of the present embodiment can reduce the measurement error attributable to the accuracy of the second sensor.

The method of generating and displaying a three-dimensional image with the smartphone 1 according to the present embodiment may be similar to the first embodiment. The user can more easily understand three-dimensional images visually with the smartphone 1 according to the present embodiment as well.

Third Embodiment

In the third embodiment, the entire first contour is estimated from a portion of a calculated first contour. Furthermore, a three-dimensional image is generated from the estimated value, and the generated three-dimensional image is displayed on the smartphone 1. The smartphone 1 of the present embodiment may have the same configuration as the block diagram of FIG. 22 in the second embodiment. The differences from the first and second embodiments are described below, with a description of common features being omitted.

Figure 24:
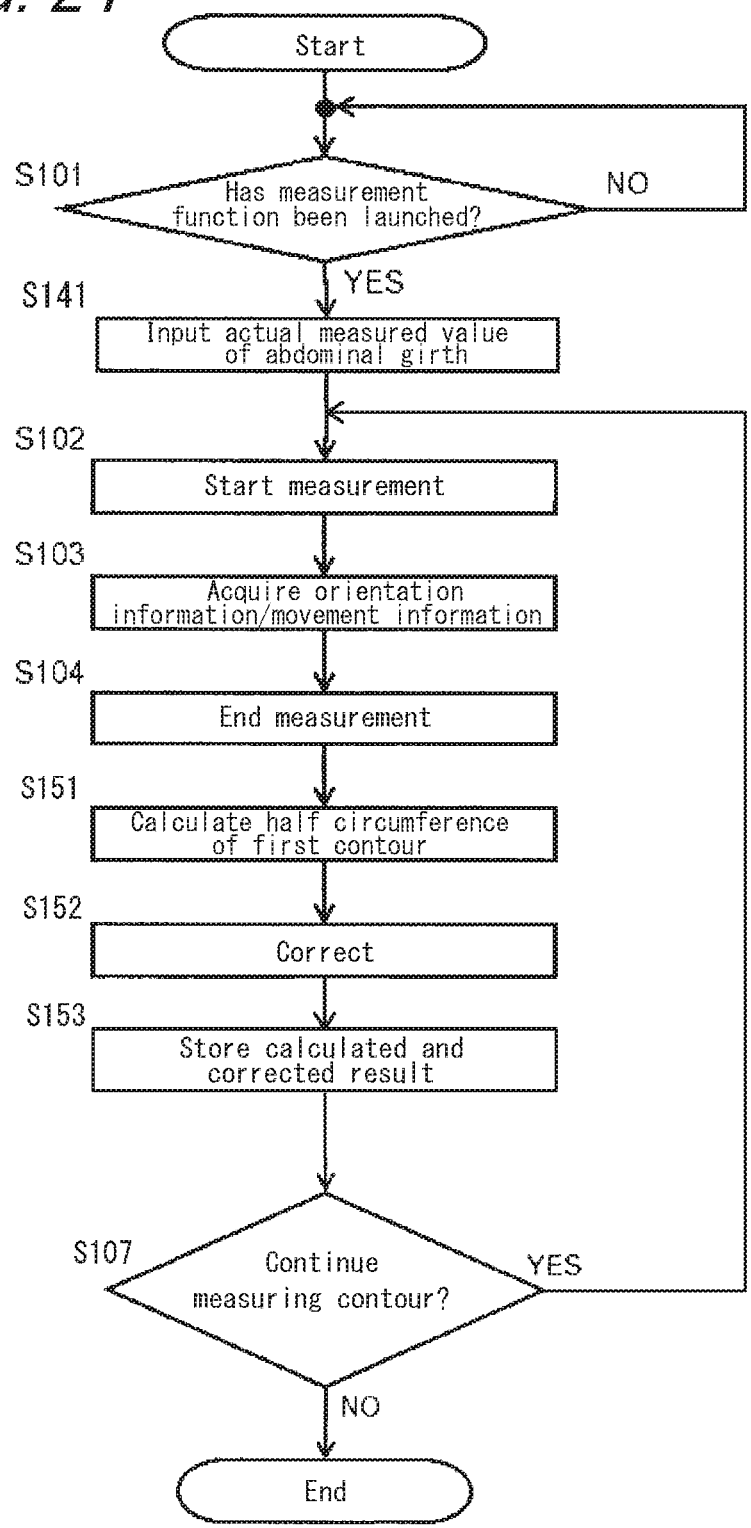
FIG. 24 is a flowchart for measuring the contour of an object according to a third embodiment.

FIG. 24 is a flowchart for measuring a first contour of an object according to the third embodiment. In the present embodiment, as an example of calculating at least a partial first contour, the case of calculating the first contour over nearly half of the circumference from the midline position of the body is described.

In step S101, the user activates the measurement function in the measurement application 9Z. After activating the measurement function in the measurement application 9Z, the user inputs the actual measured value of the abdominal girth, as measured in advance with a tape measure or other instrument, into the smartphone 1 (step S141). Alternatively, the actual measured value of the abdominal girth may be read from user information stored in advance in the storage 9 of the smartphone 1. Step S141 need not be performed before the start of measurement and may instead be performed after measurement in step S104 is complete.

Next, measurement begins in step S102. At the start of measurement, the smartphone 1 is placed against the surface of the abdomen 60 at the midline position, for example. The measurement start position may be selected in accordance with the portion of the first contour that is to be calculated. When the measurement start position is determined in advance, the range of the calculated first contour does not change from user to user, reducing the error in the below-described characteristic coefficients of the contour. In the present embodiment, the midline position is the measurement start position. For example, the side face 1C1 of the smartphone 1 is matched to the midline position, and measurement is started. The user starts measurement by performing a preset start action on the smartphone 1.

In step S103, the user moves the smartphone 1 in a first direction along the surface of the abdomen 60. The user moves the smartphone 1 at constant speed while keeping the smartphone 1 against the surface of the abdomen 60.

In step S103, the smartphone 1 acquires the angular velocity (°/s), which is orientation information, with the angular velocity sensor 18 under pre-programmed conditions. The orientation information is acquired multiple times in accordance with the clock signal outputted from the timer 11. The orientation information acquired in accordance with the clock signal is stored in the smartphone 1 along with acquired time information. This measurement is continuously made from the start of step S102 until the end of step S104.

The user moves the smartphone 1 around the abdomen 60 over half or more of the circumference at constant speed while keeping the smartphone 1 against the surface of the abdomen 60. In the present embodiment, the half circumference refers to moving from the midline to the center of the back. Accordingly, the smartphone 1 may include means for notifying the user of the half circumference.

After moving the smartphone 1 over half or more of the circumference, the user performs a preset end action on the smartphone 1 and ends measurement (step S104). Alternatively, if the below-described step S151 is executed simultaneously, the smartphone 1 may end measurement automatically by recognizing nearly half of the circumference when the orientation of the smartphone 1 changes 180° from the start of measurement. With such automatic recognition, the user need not perform the end action, which simplifies measurement.

After the end of measurement or during measurement, the control unit 10A calculates the half circumference of the first contour (step S151). The control unit 10A calculates the orientation of the smartphone 1 by integrating the angular velocity, acquired in step S103, once.

Figures 25, 26:
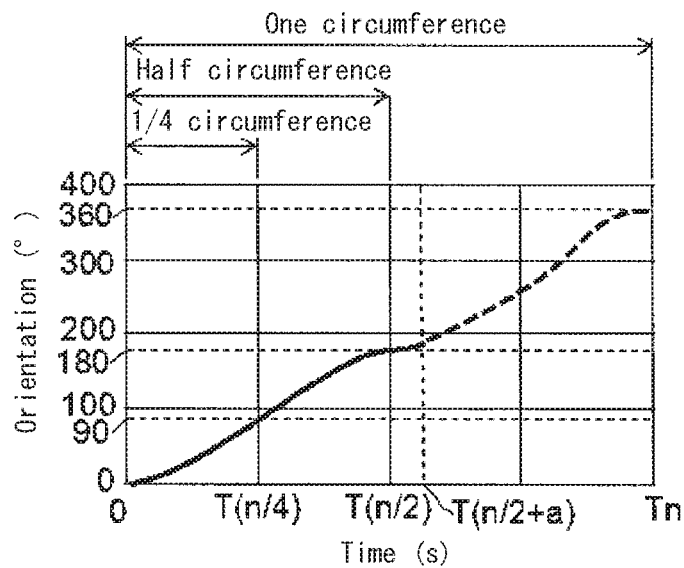
FIG. 25 illustrates an example orientation of a smartphone according to the third embodiment.
FIG. 26 is an example record formed by acquired information according to the third embodiment.

FIG. 25 illustrates an example orientation of the smartphone 1 according to the third embodiment. With reference to FIG. 25, the method of extracting information on the half circumference from the acquired orientation information is described. The horizontal axis represents time. The measurement start time is 0 s, and the measurement end time is T(n/2+a) s. Here, n represents 360° (one circumference), and a represents the angle yielded by subtracting 180° (half circumference) from the orientation at the measurement end time. The vertical axis represents the orientation of the smartphone 1. The solid line represents acquired information, whereas the dotted line is an imaginary line of non-acquired information for the full circumference. The flat portion of the curve in FIG. 25 where the orientation is near 180° is estimated to be information on the back. The smartphone 1 judges that the center of the back has been passed at the center of this flat portion and detects the half circumference. In other words, the smartphone 1 extracts the time T(n/2) s after 0 s in FIG. 25 as information on the half circumference. This method of extracting information on the half circumference is only an example. For example, when the flat portion is at a position shifted from 180°, the smartphone 1 may normalize the flat portion to 180°. The smartphone 1 may perform normalization by setting the position where the orientation is −180° from the flat portion as the starting point. Rather than the center of the flat portion, the smartphone 1 may judge that the position where the inclination of the curve is smallest near the orientation of 180° is the center of the back.

FIG. 26 is an example record formed by acquired and normalized information according to the third embodiment.

The extracted starting point of the half circumference of the contour (in the present embodiment, the position of the navel) is set to record number R0, the ending point of the half circumference (in the present embodiment, the record where the orientation is 180° at the center of the back) is set to record R(n/2), and the last acquired information is set to record R(n/2+a). In each record, orientation information and movement information are stored as a pair. The movement information is the movement amount estimated from the record number (or the time), which is clock information. In the present embodiment, records for an orientation of 0° to 180° are extracted as information on the half circumference. Half of the actual measured value of the user's abdominal girth is stored as the movement information of record number R(n/2). The time intervals between records are equal intervals, and the smartphone 1 is considered to move at a constant speed. Therefore, the interval between each movement amount, which is movement information, is also an equal interval. Records acquired in this way are displayed as a diagram indicating the half circumference of the first contour. The smartphone 1 can calculate the half circumference of the first contour of the object by plotting the xy coordinates of the acquired records R0 to R(n/2) in order in accordance with orientation and movement amount. Step S151 may be executed in parallel with step S103.

In step S152, the smartphone 1 corrects the results of the calculations in step S151. The orientation of the contour and the position of the contour may be corrected based on an inverted closed curve yielded by folding the calculated half circumference of the first contour over an axis of symmetry defined by a line connecting the starting point (the midline position in the present embodiment) and the ending point (the center of the back in the present embodiment). To correct the orientation of the contour, the inverted closed curve may be rotated so that the axis of symmetry of the inverted closed curve (the line connecting the midline and the center of the back) faces a predetermined direction. To correct the position of the contour, the inverted closed curve may be moved so that the center point of the inverted closed curve coincides with the origin of the coordinate system. The orientation and position may be corrected by a known method.

Figure 27:
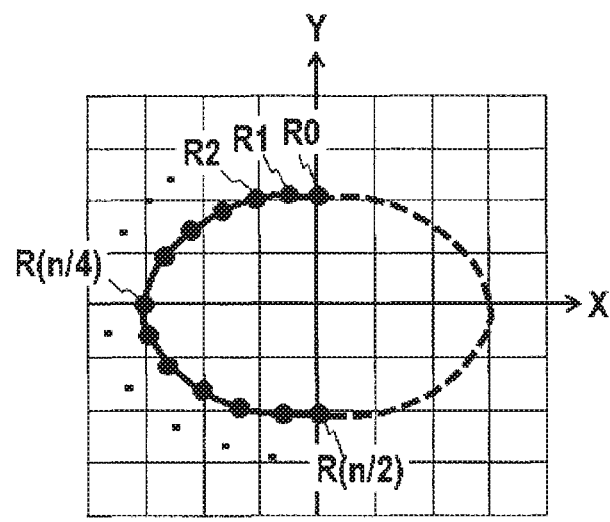
FIG. 27 illustrates a first contour calculated and corrected in the third embodiment.

FIG. 27 illustrates a calculated and corrected first contour according to the third embodiment. The solid line in the graph is the calculated half circumference of the first contour, and the dotted line is the imaginary line when the calculated half circumference of the first contour is rotated about the axis of symmetry. The black dots are plots of the acquired records on the xy coordinates. The controller 10 can derive the first contour in this way.

In step S153, the smartphone 1 stores the results of the calculation and correction performed in steps S151 and S152 in the storage 9.

In step S107, the smartphone 1 judges whether to continue measuring the contour based on user operation input. When contour measurement is to be continued (step S107: YES), the smartphone 1 proceeds to step S102. In this case, the user can measure the first contour by placing the smartphone 1 against the abdomen 60 at a different height and moving the smartphone 1 in the first direction.

When contour measurement is not to be continued (step S107: NO), the smartphone 1 ends the processing flow.

The second contour may be measured in the same way as with the method described in the first embodiment. The method of generating and displaying a three-dimensional image with the smartphone 1 according to the present embodiment may be similar to the first embodiment. The user can more easily understand three-dimensional images visually with the smartphone 1 according to the present embodiment as well.

The first contour of a human is nearly symmetrical. Therefore, by simply calculating at least the half circumference of the first contour, the smartphone 1 of the present embodiment can estimate the entire first contour. As a result, it suffices for the user to move the smartphone 1 around at least half of the abdomen, thereby shortening the measurement time. Furthermore, the smartphone 1 no longer needs to be switched between hands during measurement, making it easier to move the smartphone 1 at a constant speed and improving measurement accuracy.

Instead of calculating the first contour from the half circumference, the smartphone 1 may calculate the first contour from a ¼ circumference. For example, the case of calculating the first contour based on the ¼ circumference from the midline to the side is described. The process is similar to the above-described process of FIG. 24, replacing the half circumference with a ¼ circumference. To calculate the ¼ circumference in step S151, a substantially ¼ circumference may be judged when the orientation of the smartphone 1 has changed 90° from the start of measurement, for example. It is judged that the ¼ circumference point has been passed at an orientation of 90° in the graph of the orientation of the smartphone 1 in FIG. 25, and a ¼ circumference is detected. In other words, the portion from 0 s to T(n/4) s in FIG. 25 is extracted as information on the ¼ circumference. The records for the orientation from 0° to 90° in FIG. 26 are extracted as information on the ¼ circumference. In the example records of FIG. 26, the ending point of the ¼ circumference is record R(n/4). One quarter of the actual measured value of the user's abdominal girth is stored as the movement information of record number R(n/4). The smartphone 1 moves at a constant speed. The interval between each movement amount, which is movement information, is therefore also an equal interval. The ¼ circumference of the first contour of the object can be calculated by plotting the records R0 to R(n/4) acquired in this way in order, in accordance with orientation and movement amount. The orientation and position of the contour can easily be corrected in step S152 based on the inverted closed curve yielded by folding the calculated ¼ circumference of the contour over axes of symmetry defined by the y-axis and x-axis of the coordinate system. In this case, the estimation formula in the above-described FIG. 17 may be derived by changing the half circumference to a ¼ circumference. This method of extracting the ¼ circumference is only an example. When the time at which the orientation becomes 180° is T(n/2), for example, the record at half of that time may be extracted as the ¼ circumference.

In this case, the smartphone 1 can estimate the first contour by calculating at least a ¼ circumference of the first contour. As a result, it suffices for the user to move the smartphone 1 around at least ¼ of the abdomen, thereby shortening the measurement time. Furthermore, the smartphone 1 no longer needs to be circled around to the back during measurement, making it easier to move the smartphone 1 at a constant speed and further improving measurement accuracy.

The ¼ circumference from the midline to the side has been illustrated in the present embodiment, but the present disclosure is not limited to this example. The first contour can be estimated by calculating the ¼ circumference from near the side to the back.

Figure 28:
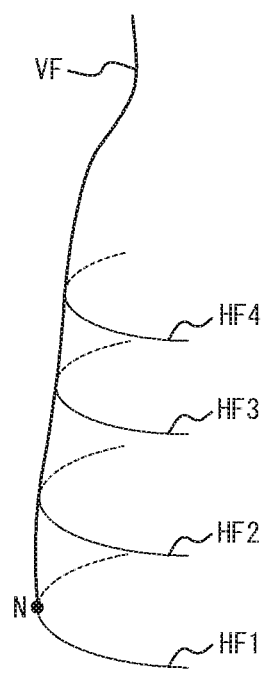
FIG. 28 illustrates an example display by the smartphone according to the third embodiment.

When calculating the first contour based on the ¼ circumference from the midline to the side, the smartphone 1 need not necessarily calculate the entire first contour. The smartphone 1 may, for example, calculate only the front side of the user's first contour. In this case, the smartphone 1 can perform corrections based on the inverted curve yielded by folding the calculated ¼ circumference of the contour over the y-axis of the coordinate system as an axis of symmetry. The smartphone 1 may, in this case, generate a three-dimensional image based on a first contour showing only the front side and the second contour, for example. The smartphone 1 generates the three-dimensional image illustrated in FIG. 28, for example, and outputs the three-dimensional image to the display 2A in this case. The smartphone 1 can thereby display a three-dimensional image of only the front side of the object. When the object is the abdomen of the body, the front side tends to change more than the back side. The user can therefore visually understand the three-dimensional image even when only the front side is displayed.

In the present embodiment, the smartphone 1 can estimate the first contour even when the orientation information and the movement information are acquired for less than the half circumference of the abdomen. For example, the smartphone 1 may estimate the first contour based on contour information from the midline position to the 135° position (⅜ of the circumference).

Next, a system according to an embodiment of the present disclosure is described in detail with reference to the drawings.

Figure 29:
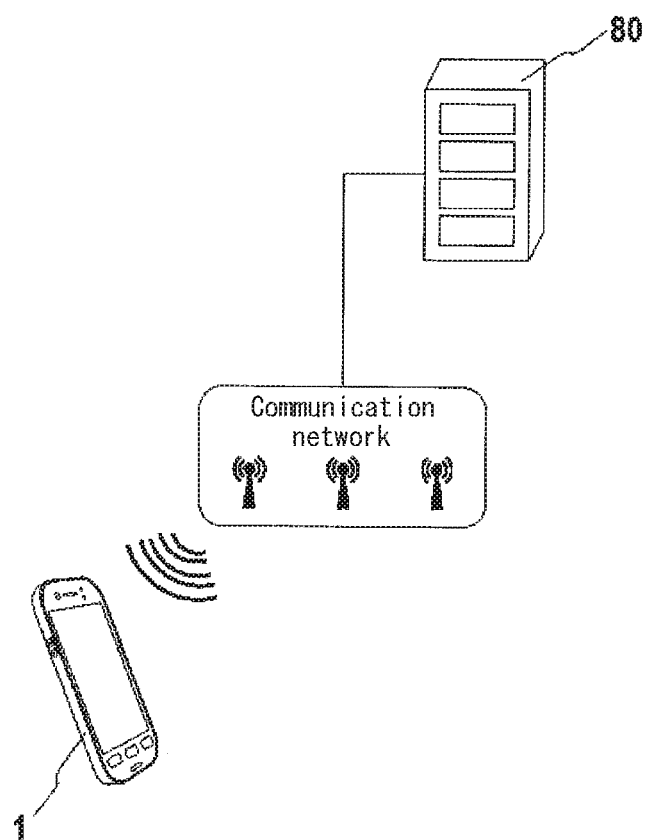
FIG. 29 conceptually illustrates a device and a system according to an embodiment, the device including a communication interface.

The system according to the present embodiment in FIG. 29 includes a server 80, a smartphone 1, and a communication network. As illustrated in FIG. 29, the smartphone 1 transmits the calculation result of the measured first and second contours to the server 80 over a communication network. The server 80 generates a three-dimensional image based on the first and second contours and transmits the data of the generated three-dimensional image to the smartphone 1. The smartphone 1 can display the three-dimensional image transmitted from the server 80 on the display 2A. In this case, the three-dimensional image is generated on the server 80. The burden of calculation on the controller 10 of the user's smartphone 1 can therefore be reduced, allowing the smartphone 1 to be reduced in size and simplified. A configuration may also be adopted to transmit the acquired orientation information, movement information, and abdominal girth to the server 80. In this case, the server 80 calculates the first and second contours. The burden of calculation on the controller 10 of the user's smartphone 1 can therefore be further reduced. The processing speed for calculation also improves.

The server 80 may store the measured first and second contours and the three-dimensional image generated based on the first and second contours. The server 80 may store at least one of the following pieces of data: a first time at which a first three-dimensional image was measured; a second time at which a second three-dimensional image was measured; the type, amount, and calories of food or drink consumed by the user between the first time and the second time; and the user's amount of exercise, calories burned, and hours of sleep. In response to a request from the smartphone 1, the server 80 may transmit a three-dimensional image and data stored at a predetermined time to the smartphone 1. The smartphone 1 may display the three-dimensional image and the data transmitted from the server 80 on the smartphone 1.

As the system according to the present embodiment, a configuration in which the smartphone 1 and the server 80 are connected over a communication network has been illustrated. The system of the present disclosure is not, however, limited to this configuration. It suffices for the system to include a measuring instrument that is moved along the surface of an object, a first sensor configured to acquire orientation information of the measuring instrument, a device configured to obtain movement information of the measuring instrument, and a controller configured to calculate a contour of the object and generate a three-dimensional image. These functional units may be connected by a communication interface.

Characteristic embodiments have been described for a complete and clear disclosure. The appended claims, however, are not limited to the above embodiments and are to be understood as encompassing all of the possible modifications and alternate configurations that a person of ordinary skill in the art could make within the scope of the fundamental features indicated in the present disclosure.

For example, in the above embodiments, the smartphone 1 has been described as generating the three-dimensional image based on the first contour and the second contour, but the smartphone 1 may generate the three-dimensional image without using the second contour. In this case, the smartphone 1 can generate the three-dimensional image by lining up first contours.

Figure 30:
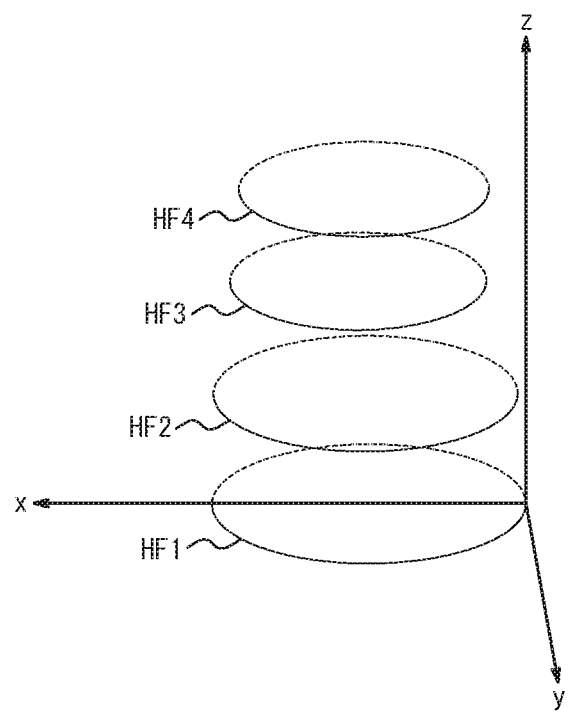
FIG. 30 illustrates a modification of a three-dimensional image.

FIG. 30 illustrates a modification of a three-dimensional image. This example three-dimensional image is generated by lining up first contours. To generate the three-dimensional image by lining up first contours, the smartphone 1 lines up a plurality of first contours in the order of measured height (in the example in FIG. 30, in the order HF1, HF2, HF3, HF4 from the bottom). In this case, the smartphone 1 may display three axes (x-axis, y-axis, z-axis) to facilitate viewing of the three-dimensional image.

The smartphone 1 may generate the three-dimensional image by lining up a plurality of first contours so that the centers of the first contours coincide in the z-axis direction. The smartphone 1 may generate the three-dimensional image by lining up a plurality of first contours so that the centers at the back of the first contours coincide in the z-axis direction.

In the above embodiments, the case of the electronic device being the smartphone 1 has been described, but the electronic device of the present disclosure is not limited to the smartphone 1 and simply needs to include the first sensor, the device, and the controller. Furthermore, the first sensor, the device, and the controller need not be provided inside the electronic device and may be separate, individual components.

In the above embodiments, the case of generating a three-dimensional image of the body has been described. The three-dimensional image is not limited to the body, however, and may also be generated for the thigh or the like, for example. Besides a human body, the contour of an animal body, leg, or the like may also be measured. Three-dimensional images generated at different times may be displayed side-by-side for comparison.

In the above embodiments, the case of using the direction sensor 17 and the angular velocity sensor 18 as the first sensor has been described, but the first sensor may be any other component that can acquire orientation information of the electronic device. For example, an inclination sensor may be used as the first sensor.

The case of using the acceleration sensor 16 or the electronic tape measure 71 as the second sensor has been described, but the second sensor may be any other component that can acquire movement information of the electronic device. For example, an electronic roller distance meter that acquires movement information by detecting the number of revolutions of a wheel may be used as the second sensor.

In the above embodiments, examples of measuring the first contour of the object over one circumference, a half circumference, and a ¼ circumference have been described, but other lengths are possible. For example, the first contour may be measured around the circumference twice, and the data may be averaged to allow highly accurate measurement with less variation.

Much of the subject matter of the present disclosure is described as a series of operations executed by a computer system and other hardware that can execute program instructions. Examples of the computer system and other hardware include a general-purpose computer, a personal computer (PC), a dedicated computer, a workstation, a personal communications system (PCS), a mobile (cellular) phone, a mobile phone with a data processing function, an RFID receiver, a game device, an electronic notepad, a laptop computer, a GPS receiver, and other programmable data processing apparatuses. It should be noted that in each embodiment, various operations are executed by a dedicated circuit (for example, individual logical gates interconnected in order to execute a particular function) implementing program instructions (software), or by a logical block, program module, or the like executed by one or more processors. The one or more processors that execute a logical block, program module, or the like include, for example, one or more of a microprocessor, CPU, application specific integrated circuit (ASIC), digital signal processor (DSP), programmable logic device (PLD), field programmable gate array (FPGA), processor, controller, microcontroller, microprocessor, electronic device, other apparatus designed to be capable of executing the functions disclosed here, and/or a combination of any of the above. The embodiments disclosed here are, for example, implemented by hardware, software, firmware, middleware, microcode, or a combination of any of these. The instructions may be program code or a code segment for executing the necessary tasks. The instructions may be stored on a machine-readable, non-transitory storage medium or other medium. The code segment may indicate a combination of any of the following: procedures, functions, subprograms, programs, routines, subroutines, modules, software packages, classes, instructions, data structures, or program statements. The code segment transmits and/or receives information, data arguments, variables, or memory content to or from another code segment or hardware circuit and thereby connects to the other code segment or hardware circuit.

The network used here may, unless indicated otherwise, be the Internet, an ad hoc network, a local area network (LAN), a wide area network (WAN), a metropolitan area network (MAN), a cellular network, a wireless wide area network (WWAN), a wireless personal area network (WPAN), a public switched telephone network (PSTN), a terrestrial wireless network, another network, or a combination of any of these. The constituent elements of a wireless network for example include an access point (such as a Wi-Fi access point), a femtocell, or the like. Furthermore, a wireless communication device can connect to a wireless network that uses Wi-Fi, Bluetooth®, cellular communication technology (such as code division multiple access (CDMA), time division multiple access (TDMA), frequency division multiple access (FDMA), orthogonal frequency division multiple access (OFDMA), or single-carrier frequency division multiple access (SC-FDMA)), or other wireless techniques and/or technical standards. One or more techniques may be adopted for the networks. Such techniques include, for example, Universal Mobile Telecommunications System (UTMS), Long Term Evolution (LTE), Evolution-Data Optimized or Evolution-Data Only (EV-DO), Global System for Mobile Communications (GSM®) (GSM is a registered trademark in Japan, other countries, or both), Worldwide Interoperability for Microwave Access (WiMAX), Code Division Multiple Access-2000 (CDMA-2000), or Time Division Synchronous Code Division Multiple Access (TD-SCDMA).

The circuit configuration of the communication interface or other such components provides functionality by using a variety of wireless communication networks, such as WWAN, WLAN, and WPAN. The WWAN may be a network such as a CDMA network, a TDMA network, an FDMA network, an OFDMA network, or a SC-FDMA network. The CDMA network implements one or more Radio Access Technologies (RAT), such as CDMA2000 and Wideband-CDMA (W-CDMA). CDMA2000 includes the IS-95, IS-2000, and IS-856 standards. The TDMA network can implement GSM®, Digital Advanced Phone System (D-AMPS), or another RAT. GSM® and W-CDMA are listed in documents issued by the consortium known as 3rd Generation Partnership Project (3GPP). CDMA2000 is listed in documents issued by the consortium known as 3rd Generation Partnership Project 2 (3GPP2). The WLAN may be an IEEE802.11x network. The WPAN may be a Bluetooth® network, an IEEE802.15x network, or other type of network. CDMA may be implemented as a wireless technique such as Universal Terrestrial Radio Access (UTRA) or CDMA2000. TDMA may be implemented by a wireless technique such as GSM®/General Packet Radio Service (GPRS)/Enhanced Data Rates for GSM® Evolution (EDGE). OFDMA may be implemented by wireless techniques such as Institute of Electrical and Electronics Engineers (IEEE) 802.11 (Wi-Fi), IEEE802.16 (WiMAX), IEEE802.20, or Evolved UTRA (E-UTRA). These techniques may be used in a combination of any of WWAN, WLAN, and/or WPAN. These techniques may also be implemented in order to use an Ultra Mobile Broadband (UMB) network, a High Rate Packet Data (HRPD) network, a CDMA20001× network, GSM®, Long Term Evolution (LTE), or the like.

The storage 9 used here may also be configured by a computer-readable, tangible carrier (medium) in the categories of solid-state memory, magnetic disks, and optical discs. Data structures and an appropriate set of computer instructions, such as program modules, for causing a processor to execute the techniques disclosed herein are stored on these media. Examples of computer-readable media include an electrical connection with one or more wires, a magnetic disk storage medium, a magnetic cassette, a magnetic tape, or other magnetic or optical storage medium (such as a Compact Disc (CD), laser Disc®, DVD®, Floppy® disk, and Blu-ray® Disc (laser disc and floppy are registered trademarks in Japan, other countries, or both)), portable computer disk, random access memory (RAM), read-only memory (ROM), rewritable programmable ROM such as EPROM, EEPROM, or flash memory, another tangible storage medium that can store information, or a combination of any of these. The memory may be provided internally and/or externally to a processor or processing unit. As used in the present disclosure, the term "memory" refers to all types of long-term storage, short-term storage, volatile, non-volatile, or other memory. No limitation is placed on the particular type or number of memories, or on the type of medium for memory storage.

While the disclosed system has a variety of modules and/or units for implementing particular functions, these modules and units have only been indicated schematically in order to briefly illustrate the functionality thereof. It should be noted that no particular hardware and/or software is necessarily indicated. In this sense, it suffices for the modules, units, and other constituent elements to be hardware and/or software implemented so as to substantially execute the particular functions described herein. The various functions of different constituent elements may be implemented by combining or separating hardware and/or software in any way, and the functions may each be used individually or in some combination. An input/output (I/O) device or user interface including, but not limited to, a keyboard, display, touchscreen, or pointing device may be connected to the system directly or via an I/O controller. In this way, the various subject matter disclosed herein may be embodied in a variety of forms, and all such embodiments are included in the scope of the subject matter in the present disclosure.

The invention claimed is:

1. An electronic device comprising:
    a measurement unit configured to measure a contour of a body by the electronic device being moved along a surface of the body; and
    a controller configured to generate a three-dimensional image of the body based on the contour by lining up a plurality of first contours measured along a first direction,
    wherein the controller is further configured to extract a characteristic coefficient of the contour and estimate a fat area in the body based on the characteristic coefficient.

2. The electronic device of claim 1, wherein the controller is configured to generate the three-dimensional image by crossing the plurality of first contours with a second contour acquired along a second direction different from the first direction.

3. The electronic device of claim 2, wherein the first direction and the second direction are substantially orthogonal to each other.

4. The electronic device of claim 2,
    wherein at least one of the plurality of first contours and the second contour each include an umbilical portion; and
    wherein the controller is configured to generate the three-dimensional image by crossing the umbilical portion of the at least one of the plurality of first contours with the umbilical portion of the second contour.

5. The electronic device of claim 1, wherein the three-dimensional image comprises a three-dimensional wire frame image.

6. The electronic device of claim 1, wherein the controller is configured to display a first three-dimensional image and a second three-dimensional image, generated based on contours measured at different times, side-by-side on a display.

7. The electronic device of claim 6, wherein the controller is configured to determine the first three-dimensional image and the second three-dimensional image based on user selection.

8. The electronic device of claim 1, wherein the measurement unit comprises at least one of an acceleration sensor, a direction sensor, an angular velocity sensor, and an inclination sensor.

9. The electronic device of claim 1, wherein the body comprises an abdomen.

10. A display method, the display method comprising:
    measuring a contour of a body by an electronic device being moved along a surface of the body;
    generating a three-dimensional image of the body by lining up a plurality of first contours measured along a first direction;
    extracting a characteristic coefficient of the contour; and
    estimating a fat area in the body based on the characteristic coefficient.

11. A generation system comprising:
    a measurement unit configured to measure a contour of a body by a device being moved along a surface of the body; and
    a controller configured to generate a three-dimensional image of the body based on the contour by lining up a plurality of first contours measured along a first direction,
    wherein the controller is further configured to extract a characteristic coefficient of the contour and estimate a fat area in the body based on the characteristic coefficient.

12. The electronic device of claim 1, further comprising:
    a timer configured to output a clock signal,
    wherein the measurement unit is configured to measure the contour in accordance with the clock signal.

13. The display method of claim 10, wherein the contour is measured in accordance with a clock signal.

14. The generation system of claim 11, further comprising:
    a timer configured to output a clock signal,
    wherein the measurement unit is configured to measure the contour in accordance with the clock signal.

* * * * *